United States Patent
Marx et al.

(10) Patent No.: US 10,945,946 B2
(45) Date of Patent: Mar. 16, 2021

(54) SYNTHESIS AND APPLICATION OF MICROBUBBLE-FORMING COMPOUNDS

(71) Applicant: California Institute of Technology, Pasadena, CA (US)

(72) Inventors: Vanessa M. Marx, Pasadena, CA (US); Robert H. Grubbs, South Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 6 days.

(21) Appl. No.: 16/831,781

(22) Filed: Mar. 26, 2020

(65) Prior Publication Data

US 2020/0222311 A1 Jul. 16, 2020

Related U.S. Application Data

(62) Division of application No. 15/737,705, filed as application No. PCT/US2016/038428 on Jun. 20, 2016, now Pat. No. 10,646,432.

(60) Provisional application No. 62/181,646, filed on Jun. 18, 2015.

(51) Int. Cl.
| | |
|---|---|
| *A61K 9/00* | (2006.01) |
| *C07F 9/38* | (2006.01) |
| *A61K 9/107* | (2006.01) |
| *A61K 31/663* | (2006.01) |
| *A61K 9/12* | (2006.01) |
| *A61N 5/02* | (2006.01) |
| *A61N 7/02* | (2006.01) |
| *C07B 41/12* | (2006.01) |
| *C07B 43/06* | (2006.01) |
| *A61N 7/00* | (2006.01) |

(52) U.S. Cl.
CPC ............ *A61K 9/0009* (2013.01); *A61K 9/107* (2013.01); *A61K 9/1075* (2013.01); *A61K 9/12* (2013.01); *A61K 31/663* (2013.01); *A61N 5/02* (2013.01); *A61N 7/02* (2013.01); *C07B 41/12* (2013.01); *C07B 43/06* (2013.01); *C07F 9/3873* (2013.01); *A61N 2007/0004* (2013.01); *A61N 2007/0039* (2013.01)

(58) Field of Classification Search
CPC .... A61K 9/0009; A61K 31/663; A61K 9/107; A61K 9/12; A61K 9/1075; C07B 43/06; C07B 41/12; A61N 7/02; A61N 5/02; A61N 2007/0039; A61N 2007/0004; C07F 9/3873; C08G 65/3355; C08G 65/3356; C08G 65/33389; C08G 65/336
See application file for complete search history.

(56) References Cited

U.S. PATENT DOCUMENTS

| | | |
|---|---|---|
| 5,463,092 A | 10/1995 | Hostetler et al. |
| 6,245,318 B1 | 6/2001 | Klibanov et al. |
| 6,261,537 B1 | 7/2001 | Klaveness et al. |
| 2007/0110674 A1 | 5/2007 | Xu et al. |
| 2007/0207194 A1 | 9/2007 | Grayburn et al. |
| 2007/0258908 A1 | 11/2007 | Lanza et al. |
| 2008/0045865 A1 | 2/2008 | Kislev |
| 2008/0269668 A1 | 10/2008 | Keenan et al. |
| 2008/0319375 A1 | 12/2008 | Hardy |
| 2009/0136594 A1 | 5/2009 | McLeroy et al. |
| 2009/0215729 A1 | 8/2009 | Johnson et al. |
| 2013/0123781 A1 | 5/2013 | Grubbs et al. |
| 2019/0282695 A1 | 9/2019 | Grubbs et al. |

FOREIGN PATENT DOCUMENTS

| | | |
|---|---|---|
| EP | 2468760 A1 | 6/2012 |
| JP | 2009-280500 A | 12/2009 |
| WO | WO 01/09146 A1 | 2/2001 |
| WO | WO 2008/131217 A1 | 10/2008 |
| WO | WO 2009/055014 A2 | 4/2009 |
| WO | WO 2009/141823 A2 | 11/2009 |
| WO | WO 2012/094541 A2 | 7/2012 |
| WO | WO 2012/143739 A1 | 10/2012 |

OTHER PUBLICATIONS

Bhadane, S., "High Intensity Focused Ultrasound and Microbubble Induced Tissue Ablation: Effect of Treatment Parameters on Thermal Lesion Volume and Temperature," Thesis, Ryerson University, 2009, 104 Pages.
Bhushan, K. R., et al., "Synthesis of Conjugatable Bisphosphonates for Molecular Imaging of Large Animals," Angewandte Chemie International Edition, 2007, pp. 7679-7971, vol. 46.
Deelman, L. E., et al., "Targeted renal therapies through microbubbles and ultrasound," *Advanced Drug Delivery Reviews*, 2010, pp. 1369-1377, vol. 62.
Geers, B., et al., "Adeno-associated virus loaded microbubbles as a tool for targeted gene Delivery," *Journal of Controlled Release*, 2010, 148, e57-e73, p. e59 (abstract).
Hernot, S., et al., "Microbubbles in Ultrasound-triggered drug and gene delivery," *Advanced Drug Delivery Reviews*, 2008, pp. 1153-1166, vol. 60.
Hu, Y., et al., "Mesenchymal stem cells: A promising targeted-delivery vehicle in cancer gene Therapy," *Journal of Controlled Release*, 2010, pp. 154-162, vol. 147.
Khelfallah, S. K., et al., "Synthesis of novel polymerizable molecules bearing bisphosphonate," *Organic & Biomolecular Chemistry*, 2015, pp. 11382-11392, vol. 13.

(Continued)

*Primary Examiner* — Hasan S Ahmed
(74) *Attorney, Agent, or Firm* — Fenwick & West LLP

(57) ABSTRACT

The present disclosure is directed to fatty-acid glycerol ester derivative compounds containing a targeting bisphosphonate group. The disclosure further include pharmaceutical or biomedical compositions comprising these compounds, and methods of using these compounds and compositions forming microbubbles. The microbubbles have affinity for metal-containing, especially calcium-containing, bodies and/or biological targets. In certain embodiments, these compositions are useful for providing targeted placement of microbubbles capable of cavitation on application of high frequency energy.

8 Claims, 4 Drawing Sheets

(56) References Cited

OTHER PUBLICATIONS

Liu, Y., et al., "Encapsulated ultrasound microbubbles: Therapeutic application in drug/gene Delivery," *Journal of Controlled Release*, 2006, pp. 89-99, vol. 114.
Matheson Tri-Gas, Inc., "Material Safety Data Sheet, Substance: Perfluoropropane," 1989, [online] [Retrieved on Sep. 22, 2016] Retrieved from the Internet <URL: https://www.mathesongas.com/pdfs/msds/MAT18290.pdf>.
Mayer, C. R., et al., "Ultrasonic gene and drug delivery to the cardiovascular system," *Advanced Drug Delivery Reviews*, 2008, pp. 1177-1192, vol. 60.
McDonald, C. J., et al., "Hollow latex particles: synthesis and applications," *Advanced in Colloid and Interface Science*, 2002, pp. 181-213, vol. 99.
Mellema, M. et al., "PD22-11 Absence of Ureteral/Renal Injury Following Low Intensity Extracorporeal Acoustic Energy Lithotripsy With Stone-Targeting Microbubbles in an In Vivo Swine Model," *The Journal of Urology*, vol. 199, Issue 4S, Supplement, May 19, 2018, p. e479.
PCT International Search Report and Written Opinion, International Application No. PCT/US2016/038428, dated Oct. 27, 2016, 16 Pages.
PCT International Search Report and Written Opinion, International Application No. PCT/US2012/052187, dated Jan. 28, 2013, 11 Pages.
PCT Invitation to Pay Additional Search Fees, International Application No. PCT/US2012/052187, dated Nov. 8, 2012, 2 Pages.
Pishchalnikov, Y. et al., "Experimental observations and numerical modeling of lipid-shell microbubbles with calcium-adhering moieties for minimally-invasive treatment of urinary stones," *Proceedings of Meetings on Acoustics*, vol. 35, 020008, Nov. 2018, pp. 1-11.
Ramaswamy, K. et al., "Targeted Microbubbles: A Novel Application for the Treatment of Kidney Stones," BJU International, 2015, John Wiley & Sons Ltd., pp. 9-16, vol. 116.
Rapoport, N. et al., "Multifunctional Nanoparticles for Combining Ultrasonic Tumor Imaging and Targeted Chemotherapy," Journal Natl. Cancer. Inst., Jul. 18, 2007, vol. 99, Issue 14, pp. 1095-1106.
Shi, Y., et al., "Multistep Targeted Nano Drug Delivery System Aiming at Leukemic Stem Cells and Minimal Residual Disease," Mol. Pharmaceutics, 2013, pp. 2479-2489, vol. 10.
Sirsi, S. et al., "Microbubble Compositions, Properties and Biomedical Applications," Bubble Sci. Eng. Technol., Nov. 2009, pp. 3-17, vol. 1, No. 1-2.
Tinkov, S., et al., "New doxorubicin-loaded phospholipid microbubbles for targeted tumor therapy: Part I—Formulation development and in-vitro characterization," Journal of Controlled Release, 2010, pp. 143-150, vol. 143.
Unger, E. C. et al., "Therapeutic applications of microbubbles," European Journal of Radiology, vol. 42, Iss. 2, May 2002, pp. 160-168.
Unger, E. C., et al., "Therapeutic applications of lipid-coated microbubbles," Advanced Drug Delivery Reviews, 2004, pp. 1291-1314, vol. 56.
Vachal, P. et al., "Synthesis and Study of Alendronate Derivatives as Potential Prodrugs of Alendronate Sodium for the Treatment of Low Bone Density and Osteoporosis," *Journal of Medicinal Chemistry*, vol. 49, Iss. 11, 2006, pp. 3060-3063.
Wu, T.Y. et al., "Advances in Ultrasound Technology for Environmental Remediation," SpringerBriefs in Green Chemistry for Sustainability, 2013, pp. 5-12.
Yoshizawa, S. et al., "High Intensity Focused Ultrasound Lithotripsy with Cavitating Microbubbles," Med. Biol. Eng. Comput., 2009, pp. 851-860, vol. 47.
Chen et al., "Bone Targeted Delivery of SDF-1 via Alendronate Functionalized Nanoparticles in Guiding Stem Cell Migration," ACS Applied Materials & Interfaces (2018), vol. 10, Issue 28, p. 23700-23710.
International Search Report and Written Opinion, Patent Cooperation Treaty Application No. PCT/US2020/015493, dated Apr. 14, 2020, 13 pages.

SYNTHESIS AND APPLICATION OF MICROBUBBLE-FORMING COMPOUNDS

CROSS REFERENCE TO RELATED APPLICATIONS

This application is a divisional of U.S. application Ser. No. 15/737,705, filed Dec. 18, 2017, which is the National Stage of International Application No. PCT/US2016/038428, filed Jun. 20, 2016, which claims the benefit of U.S. Provisional Application No. 62/181,646, filed Jun. 18, 2015, each of which is incorporated by reference in its entirety.

STATEMENT OF GOVERNMENT SUPPORT

This invention was made with government support under Grant No. CHE1212767 awarded by the National Science Foundation. The government has certain rights in the invention.

BACKGROUND OF THE INVENTION

Field of the Invention

The present disclosure is generally directed to fatty-acid glycerol ester derivative compounds, methods of synthesizing such compounds and methods of using such compounds for medical treatments.

Description of the Related Art

Cavitation is a component of some currently used medical therapies. Cavitation therapy is useful as a treatment for kidney stones. Extracorporeal shock wave lithotripsy utilizes shock waves that are focused onto a stone in the kidney or ureter. The interaction between the waves and the stone induces the formation of bubbles. The collapse of these bubbles will release energy to the stone, and fragment the stone into pieces small enough to be passed via the ureter.

A large number of medical conditions are characterized, at least in part, by the presence of an obstruction or abnormal mass. Examples include urinary stones, biliary stones, blood clots, fibroids, cancerous tumors, and atheromatous plaques. Destruction or reduction of this mass without injury to healthy tissue is a goal for many treatments. Minimally invasive treatments are preferred since they reduce the pain, discomfort, and risks associated with surgical or other invasive treatments.

There have been efforts regarding use of microbubbles for the minimally invasive treatments. For instance, U.S. Publication No. 2013/0123781, titled "Targeting Microbubbles," discusses compositions comprising a bubble forming material that are "useful for providing targeted placement of microbubbles capable of cavitation on application of high frequency energy."

Despite the efforts disclosed to develop such technology, there remains a need in the art for improved bubble-forming compounds, methods for making such compounds and methods for their use.

SUMMARY OF THE INVENTION

The disclosure is directed to a series of fatty-acid glycerol ester derivative compounds.

The compounds are useful in pharmaceutical or biomedical compositions. In particular, pharmaceutical compositions of the present disclosure comprise microbubbles. These microbubbles have an affinity to metal-containing, especially calcium-containing, bodies/physiological plaques and/or biological targets. Thus, compounds of the present disclosure are broadly effective in treating a host of conditions or symptoms affected at least in part by the presence of an abnormal mass, for example, kidney stones, urinary stones, biliary stones, blood clots, fibroids, cancerous tumors, and atheromatous plaques.

In one aspect, the disclosure provides one or more compounds of formula (I) or formula (Ia):

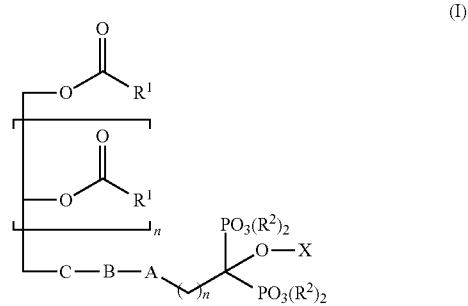

(I)

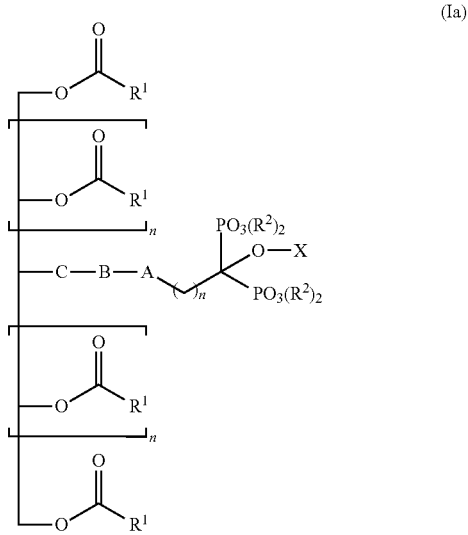

(Ia)

wherein:
each n is independently selected from 0-7;
each $R^1$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl;
each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

C is selected from the group consisting of:

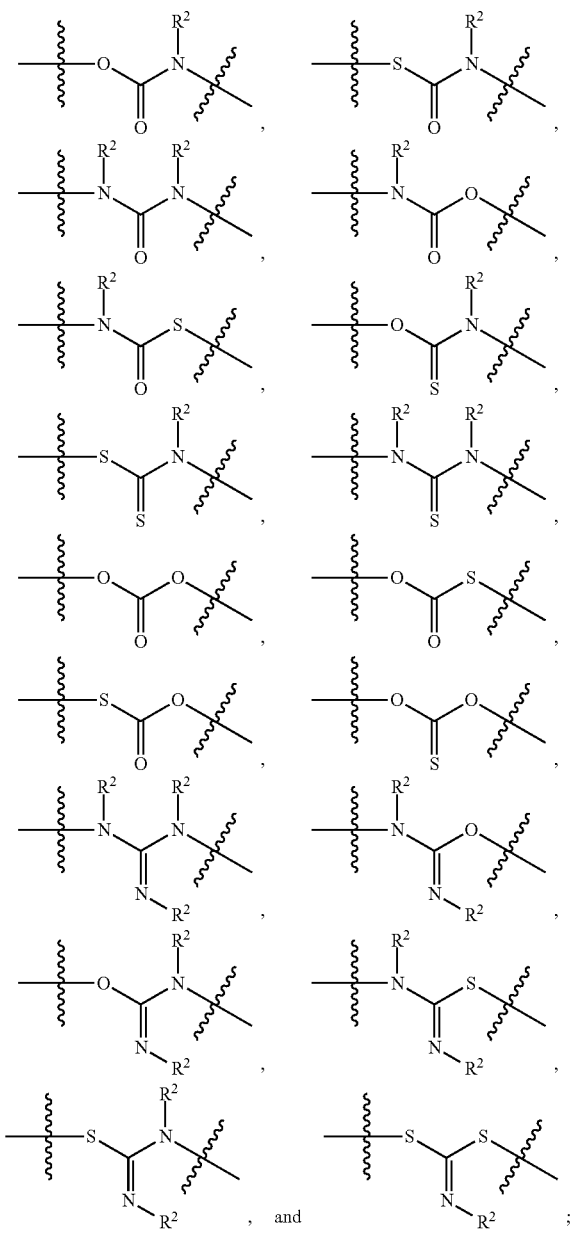

B is selected from the group consisting of: a covalent bond, ethylene glycol, and polyethylene glycol;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester, wherein any of these functional groups listed for A may be covalently bonded on either side to the

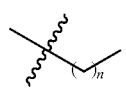

moiety;

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

or a tautomer and/or a pharmaceutically acceptable salt thereof.

In other aspects, the disclosure provides for microbubbles comprising one or more compounds described herein. The microbubbles bind to physiological plaques and/or have an affinity for metal-containing materials. In one aspect, the present disclosure provides for the selective binding of calcium-containing materials in the present of other inorganic cations, such as for example, potassium, sodium and magnesium.

In a related aspect, certain embodiments provide microbubbles further comprising fluorinated hydrocarbons, and optionally, one or more pharmaceutically acceptable excipients.

In yet another aspect, the disclosure provides methods for preparing a solution for microbubbles. In one aspect, the method comprises delivering energy to a solution comprising a bubble forming composition.

In another aspect, the disclosure provides methods for binding a physiological plaque, the method comprising delivering a composition comprising one or more compounds described herein.

In another aspect, the disclosure provides a method for treating a buildup of plaque in a subject, the method comprising:

(a) delivering a solution comprising microbubbles to a site within the subject; and (b) applying energy to the microbubbles, wherein the energy is from electromagnetic, ultrasound, microwave, or another source, in a sufficient amount to cause cavitation to form microbubbles.

In some embodiments, the energy is sufficient to cause destruction of a cell, tissue, or calculous mass at the site within the subject. In some embodiments, the energy is NOT sufficient to cause destruction of a cell, tissue, or calculous mass at the site within the subject.

These and other embodiments are described in further detail herein.

BRIEF DESCRIPTION OF THE DRAWINGS

FIG. 1A shows that microbubbles were not detected in "BLANK" A; FIG. 1B shows that the formation of microbubbles of 2-4 m diameters was detected in Example 5 with fluorocarbon gas.

FIG. 3A shows a kidney stone reacted with microbubbles formed in Solution A (9:1 DPPC:DPPA) and labelled with DiI; and FIG. 3B shows a kidney stone reacted with microbubbles formed in Solution E (VMM-iv95) and labelled with DiI.

DETAILED DESCRIPTION OF THE INVENTION

Utility

Figure 1A:
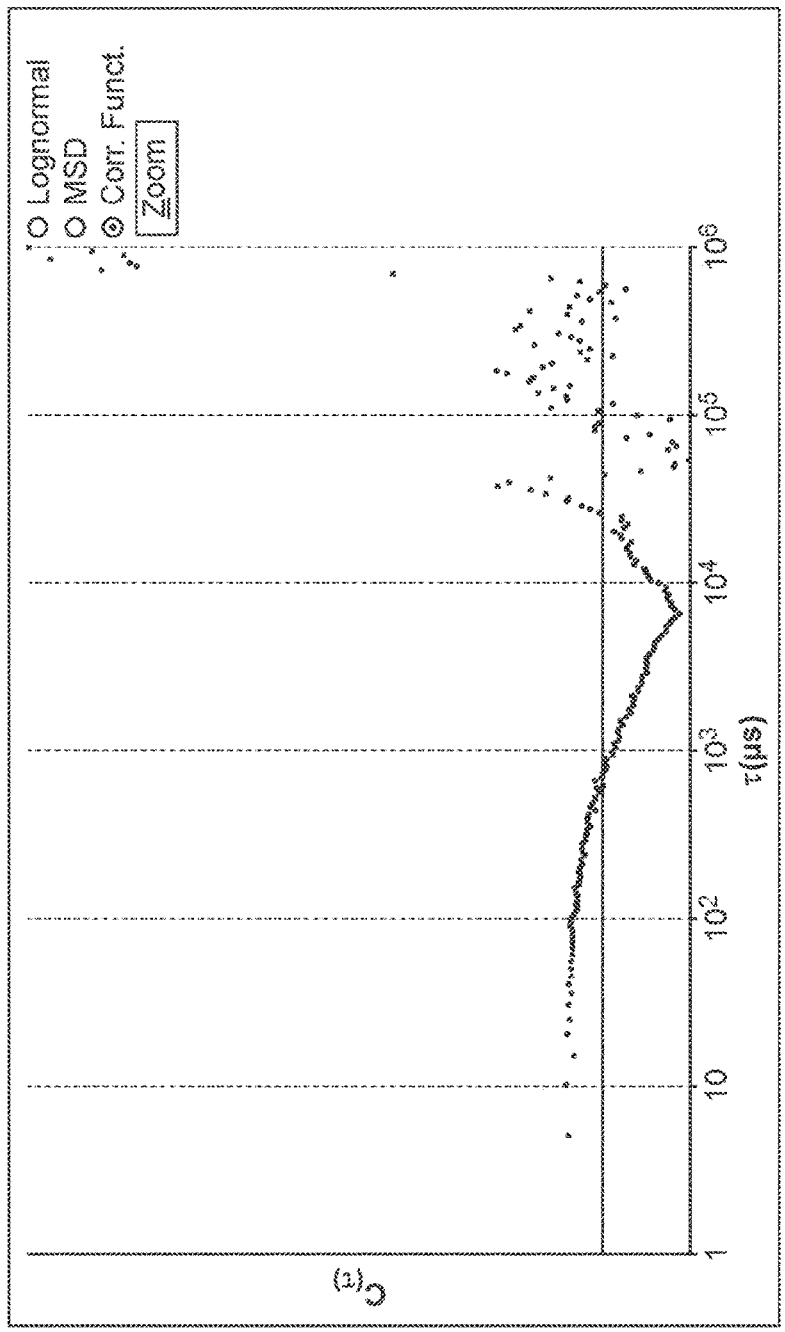
FIGS. 1A and 1B are dynamic light scattering (DLS) data from microbubble solutions: "BLANK" A Solution (9:1 DPPC:DPPA without fluorocarbon gas) and from Solution D (VMM-iv93).

Compounds of the present disclosure are fatty-acid glycerol ester derivatives useful in pharmaceutical or biomedical formulations, including compositions comprising microbubbles.

The microbubbles are capable of cavitation on application of sufficient energy. The microbubbles bind to metal-containing materials, especially calcium-containing bodies and/or biological targets. Thus, compounds of the present disclosure are useful for the treatment of a host of conditions, at least in part affected by the presence of a physiological plaque. Such conditions include, but not limited to, kidney stones, urinary stones, biliary stones, blood clots, fibroids, cancerous tumors, and atheromatous plaques.

Definitions

Terms used in the claims and specification are defined as set forth below unless otherwise specified. Further, if any term or symbol used herein is not defined as set forth below, it shall have its ordinary meaning in the art.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology can exist as solvates, especially hydrates. Hydrates may form during manufacture of the compounds or compositions comprising the compounds, or hydrates may form over time due to the hygroscopic nature of the compounds. Compounds of the present technology can exist as organic solvates as well, including DMF, ether, and alcohol solvates among others. The identification and preparation of any particular solvate is within the skill of the ordinary artisan of synthetic organic or medicinal chemistry.

"Subject" refers to a mammalian organism treated using a compound of the present disclosure. The "subject" can be a human or non-human mammalian organism.

"Tautomer" refer to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Treating" or "treatment" of a condition or symptom in a subject refers to 1) preventing the condition or symptom from occurring in a subject that is predisposed or does not yet display symptoms of the condition or symptom; 2) binding the condition or symptom or arresting its development; or 3) ameliorating or alleviating the cause of the regression of the condition or symptom.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

As used herein, the term "contacting," as used herein, includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, +100% in some aspects±50%, in some aspects±20%, in some aspects±10%, in some aspects±5%, in some aspects±1%, in some aspects±0.5%, and in some aspects±0.1% from the specified amount, as such variations are appropriate to perform the disclosed methods or employ the disclosed compositions.

"Carboxy coupling reagent (CCR)" refers to a compound that possesses a carbonyl functional group that has reactivity such that a heteroatom of a functional group may form a covalent bonding to the carbonyl, and yet after this reaction, the carbonyl functional group is sufficiently reactive to make another covalent attachment to a different heteroatom functional group. Such compounds are known in the art. Examples include, but are not limited to, phosgene, triphosgene, CDI, haloformates, and N,N'-disuccinimidyl carbonate.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Silyl" refers to silicon containing groups having the structure —$SiR_3$. Each of the three R functional groups may be the same or different and are independent selected from the group consisting of: hydrogen, halogen, alkyl, substituted alkyl, alkenyl, substituted alkenyl, alkynyl, substituted alkynyl, alkoxy, substituted alkoxy, amino, substituted amino, aryl, substituted aryl, alkyl aryl, substituted alkyl aryl, alkenyl aryl, substituted alkenyl aryl, alkynyl aryl, substituted alkynyl aryl, cycloalkyl, substituted cycloalkyl, heterocycloalkyl, substituted heterocycloalkyl, heteroaryl, and substituted heteroaryl.

"Alkenyl" refers to straight or branched hydrocarbyl groups having from 1 to 6 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

In some embodiments, the substituted alkyl groups include halogenated alkyl groups and particularly halogenated methyl groups such as trifluoromethyl, difluoromethyl, fluoromethyl and the like.

"Alkyl aryl" refers to an alkyl group having from 1 to 8, preferably 1 to 5, or more preferably 1 to 3 carbon atoms in length and is substituted specifically at any one of the carbons along the chain with an aryl group. The aryl group can include heteroatoms or not.

"Alkenyl aryl" refers to an alkenyl or alkene group having from 1 to 8, preferably 1 to 5, or more preferably 1 to 3 carbon atoms in length and is substituted specifically at any one of the carbons along the chain with an aryl group. The aryl group can include heteroatoms or not.

Alkynyl aryl" refers to an alkynyl or alkyne group having from 1 to 8, preferably 1 to 5, or more preferably 1 to 3 carbon atoms in length and is substituted specifically at any one of the carbons along the chain with an aryl group. The aryl group can include heteroatoms or not.

"Cycloalkyl" or "Cyclyl alkyl" refers to a saturated or partially saturated, but not aromatic, group having from 1 to 10 ring carbon atoms and no heteroatoms. Cycloalkyl encompasses single ring or multiple condensed rings, including fused bridged and spiro ring systems. In fused ring systems, one or more of the rings can be cycloalkyl, aryl, heterocycloalkyl, or heteroaryl provided that the point of attachment is through the original non-aromatic cycloalkyl ring.

"Substituted alkenyl" refers to alkenyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Ar" refers to any group which is aromatic. This group must be cyclic; however, it may contain heteroatoms or may not.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{30}$C(O)alkyl, —NR$^{30}$C(O)substituted alkyl, —NR$^{30}$C(O)cycloalkyl, —NR$^{30}$C(O)substituted cycloalkyl, —N R$^{30}$C(O)alkenyl, —NR$^{30}$C(O)substituted alkenyl, alkoxy, substituted alkoxy-NR$^{30}$C(O)alkynyl, —NR$^{30}$C(O)substituted alkynyl, —NR$^{30}$C(O)aryl, —NR$^{30}$C(O)substituted aryl, —NR$^{30}$C(O)heteroaryl, —NR$^{30}$C(O)substituted heteroaryl, —NR$^{30}$C(O)heterocyclic, and —NR$^{30}$C(O)substituted heterocyclic wherein R$^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the groups H—C(N)—, alkyl-C(N)—, substituted alkyl-C(N)—, alkenyl-C(N)—, substituted alkenyl-C(N)—, alkynyl-C(N)—, substituted alkynyl-C(N)—, cycloalkyl-C(N)—, substituted cycloalkyl-C(N)—, aryl-C(N)—, substituted aryl-C(N)—, heteroaryl-C(N)—, substituted heteroaryl-C(N)—, heterocyclic-C(N)—, and substituted heterocyclic-C(N)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(N)—.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{31}$R$^{32}$ where R$^{31}$ and R$^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein R$^{31}$ and R$^{32}$ are optionally joined, together with the nitrogen bound thereto to form a heterocyclic or substituted heterocyclic group, provided that R$^{31}$ and R$^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When R$^{31}$ is hydrogen and R$^{32}$ is alkyl, the substituted amino group is sometimes referred to herein as alkylamino. When R$^{31}$ and R$^{32}$ are alkyl, the substituted amino group is sometimes referred to herein as dialkylamino. When referring to a monosubstituted amino, it is meant that either R$^{31}$ or R$^{32}$ is hydrogen but not both. When referring to a disubstituted amino, it is meant that neither R$^{31}$ nor R$^{32}$ are hydrogen.

"Aminocarbonyl" refers to the group —C(O)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl carbonyloxy" refers to the group —C(NR$^{33}$)OR$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{30}$C(O)NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C(S)NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Ethylene glycol" refers to the group —O—CH$_2$CH$_2$—O-E, wherein E is either H or CH$_3$.

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In an embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. $C_x$ cycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the nonaromatic ring. In an embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiomorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O—).

"Phthalimido" refers to the group

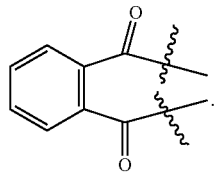 [SMILES: *C(=O)c1ccccc1C(*)=O]

Phthalimide functional groups are well known in the art and can be generated by covalently bonding a nitrogen atom to a C$_6$H$_4$(CO)$_2$ group.

"Polyethylene glycol" refers to the group —(CH$_2$CH$_2$—O)$_n$-E, wherein E is either a covalent bond, H or CH$_3$, where n is between 2-20,000. Of course, "ethylene glycol" would mean the same except that n would be 1.

"Spirocyclic ring system" refers to a ring system with two rings that has a single ring carbon atom in common to both rings. Herein used the term bicyclic can incorporate up to four heteroatoms in either ring.

"Bicyclic ring system" refers to a ring system with two rings that has two ring carbon atoms in common, and which can be located at any position along either ring. Herein used the term bicyclic ring system can incorporate up to four heteroatoms in either ring.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluoromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substitution" or "substitution" generally refers groups which are covalently bonded to an atom to replace a hydrogen atom. The atom in this general context can be a carbon atom or a heteroatom, for example a nitrogen atom.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and d or 1 enriched stereometric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Herein any substituted functional group is substituted at from one to three different positions, and those one to three substituting groups are capable of each independently being substituted at one to three positions, wherein any and each substituting group is independently selected from the group consisting of: halogen, hydroxyl, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, acyl, acylamino, aminocarbonylamino, aminoacyl, acyloxy, amino, substituted amino, aminocarbonyl, aminothiocarbonyl, aminoacyl carbonyloxy, aminocarbonylamino, aminothiocarbonylamino, aminocarbonyloxy, aminosulfonyl, aminosulfonyloxy, aminosulfonylamino, amidino, $C_1$-$C_8$ alkoxy, substituted $C_1$-$C_8$ alkoxy, $C_3$-$C_7$ aryl, substituted $C_3$-$C_7$ aryl, $C_3$-$C_7$ aryloxy, substituted $C_3$-$C_7$ aryloxy, $C_3$-$C_7$ arylthio, substituted $C_3$-$C_7$ arylthio, carboxyl, carboxyl ester, (carboxyl ester)amino, (carboxyl ester)oxy, $C_3$-$C_{10}$ cycloalkyl, substituted $C_3$-$C_{10}$ cycloalkyl, $C_3$-$C_7$ heterocycloalkyl, guanidino, substituted guanidino, $C_3$-$C_7$ heteroaryloxy, $C_3$-$C_7$ substituted heteroaryloxy, $C_3$-$C_7$ heteroarylthio, $C_3$-$C_7$ substituted heteroarylthio, sulfonyl, substituted sulfonyl, sulfinyl, substituted sulfinyl, sulfonyloxy, substituted sulfonyloxy, thioacyl, alkylthio, substituted alkylthio, $C_3$-$C_7$ heteroaryl, and substituted $C_3$-$C_7$ heteroaryl.

Herein any and all heteroaryl and heterocycloalkyl substituents may contain up to four heteroatoms selected from the group consisting of: O, N, and S.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the above definitions are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Compounds, Microbubbles & Pharmaceutical Compositions of the Present Disclosure

The disclosure is directed toward fatty-acid glycerol ester derivative compounds containing a targeting bisphosphonate group. The compounds are useful for providing microbubbles having affinity to metal-containing, specifically calcium-containing, bodies and/or biological targets and capable of cavitation on application of high frequency energy.

In some embodiments, the disclosure provides for one or more compounds of formula (II):

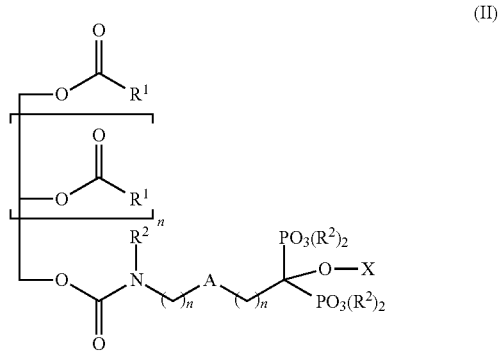

(II)

wherein:

each n is independently selected from 1-7;

each $R^1$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl;

each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester, wherein any of these functional groups listed for A may be covalently bonded on either side to either one of the

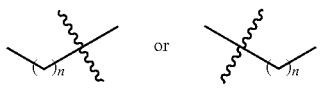

moieties;

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

or a tautomer and/or a pharmaceutically acceptable salt thereof.

In some embodiments, the disclosure provides for one or more compound of formula (III):

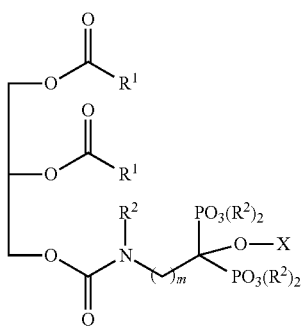

(III)

wherein:

m is from 0-26;

each $R^1$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl;

each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

or a tautomer and/or a pharmaceutically acceptable salt thereof.

In some embodiments, the disclosure provides for one or more compounds of formula (IV):

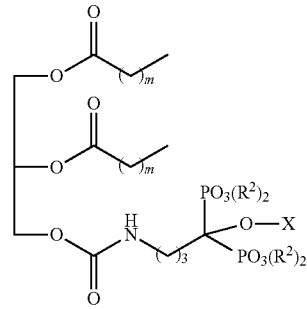

(IV)

wherein:

each m is independently selected from 7-26;

each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

or a tautomer and/or a pharmaceutically acceptable salt thereof.

In some embodiments, the disclosure provides for one or more compounds of formula (V):

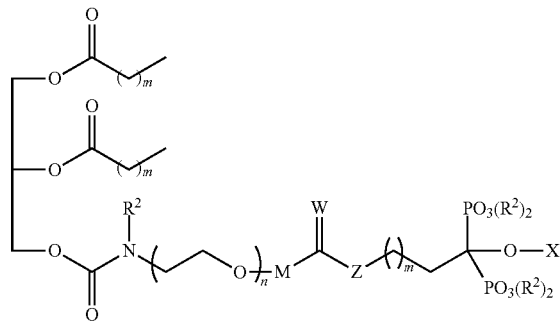

(V)

wherein:

each m is independently selected from 0-26;

n is from 1-90 each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

W is selected from the group consisting of: O, $NR^2$, and S;

each Z is independently selected from the group consisting of: a covalent bond, $CH_2$, O, $NR^2$, and S;

M is independently selected from the group consisting of: a covalent bond, $CH_2$—$CH_2$, $CH_2$—$CH_2$—Z, $CH_2$—Z and $CH_2$;

or a tautomer and/or a pharmaceutically acceptable salt thereof.

In some embodiments, the disclosure provides for a compound selected from a group consisting of:

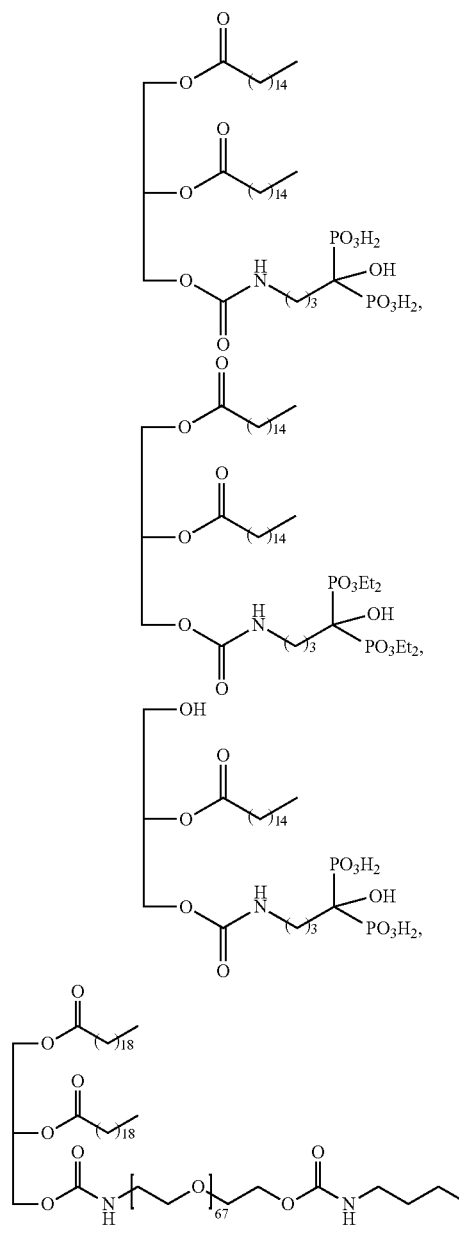

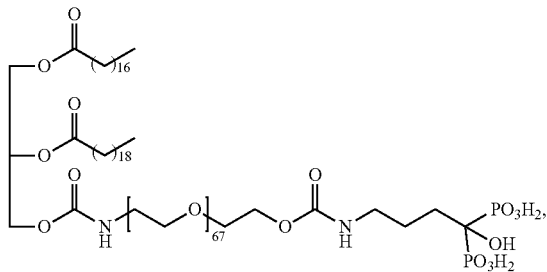

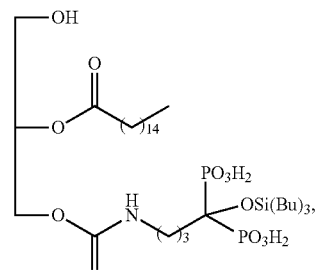

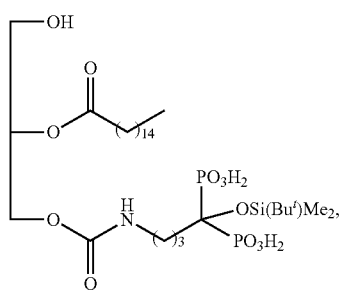

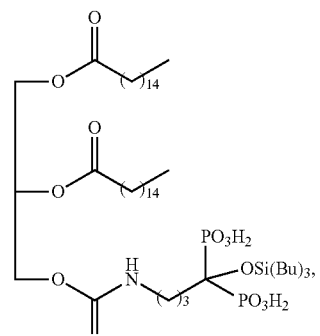

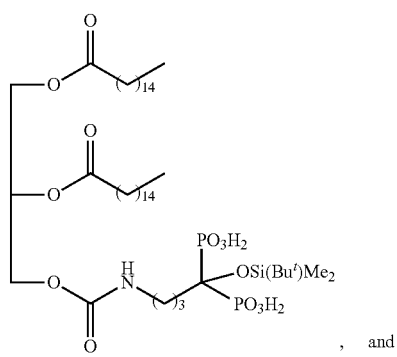

, and

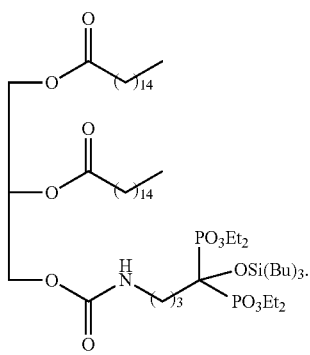

In some embodiments, the disclosure provides for a compound wherein each m is independently selected from 14-22.

In some embodiments, the disclosure provides for a compound wherein each m is independently selected from 14-22; X is silyl, and each $R^2$ is hydrogen or $C_1$-$C_8$ alkyl.

In some embodiments, the disclosure provides for a compound having the structural formula:

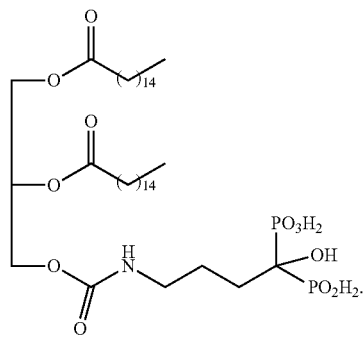

In some embodiments, the disclosure provides for a compound having the structural formula:

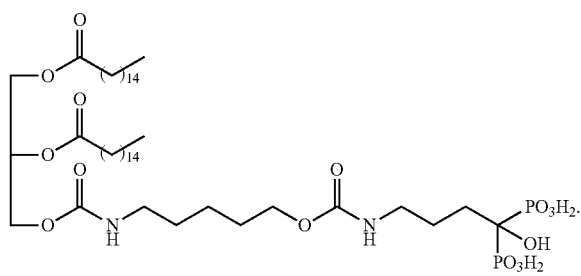

In some embodiments, the disclosure provides for a compound having the structural formula:

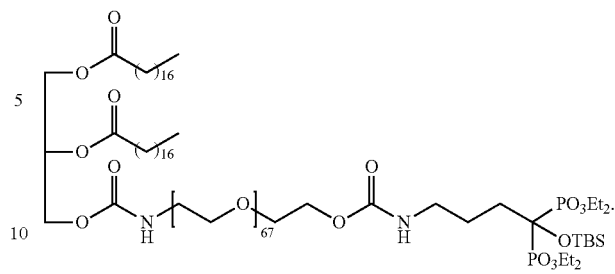

In some embodiments, the disclosure provides for a compound having the structural formula:

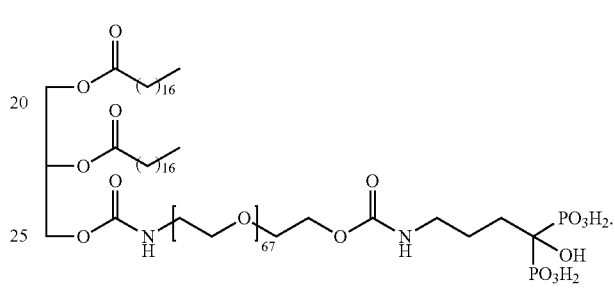

Pharmaceutical Compositions

In some embodiments, the disclosure provides for a pharmaceutical or biomedical composition comprising one or more compounds described herein.

In some embodiments, the disclosure provides for a pharmaceutical or biomedical composition wherein the composition is a suspension.

In some embodiments, the disclosure provides for a pharmaceutical or biomedical composition wherein the composition is a colloid.

In some embodiments, the disclosure provides for a pharmaceutical or biomedical composition wherein the composition is an emulsion.

In some embodiments, the disclosure provides for a pharmaceutical or biomedical composition wherein the composition is an aerosol.

In some embodiments, the disclosure provides for a pharmaceutical or biomedical composition wherein the composition is a sol.

In some embodiments, the disclosure provides for a pharmaceutical or biomedical composition wherein the composition is a gel.

In some embodiments, the disclosure provides for a pharmaceutical or biomedical composition wherein the composition is foam.

In some embodiments, the disclosure provides for a pharmaceutical composition wherein the composition is in the form of microbubbles.

In some embodiments, the disclosure provides for a pharmaceutical or biomedical composition wherein the microbubbles have a diameter of about 1 micron to about 10 microns.

In some embodiments, the disclosure provides for a pharmaceutical or biomedical composition wherein the microbubbles have an affinity for a metal-containing material.

In some embodiments, the disclosure provides for a pharmaceutical or biomedical composition wherein the metal containing material is a calcium-containing material.

In some embodiments, the disclosure provides for a pharmaceutical or biomedical composition wherein the microbubbles further comprise a core containing a fluid having a normal boiling point less than about 30° C.

In some embodiments, the disclosure provides for a pharmaceutical or biomedical composition wherein the fluid is air, $CO_2$, a fluorinated or fluorinated $C_{1-6}$ hydrocarbon, or any combination thereof.

In some embodiments, the disclosure provides for a pharmaceutical or biomedical composition wherein the fluorinated hydrocarbon is perfluoropropane or perfluoropentane.

In some embodiments, the disclosure provides for a pharmaceutical or biomedical composition wherein the composition further comprises one or more pharmaceutically acceptable excipients.

In some embodiments, the disclosure provides for a pharmaceutical or biomedical composition wherein the excipient is sterilized water.

In some embodiments, the disclosure provides for a pharmaceutical or biomedical composition wherein the excipient is a sterilized physiological fluid.

In some embodiments, the disclosure provides for a pharmaceutical or biomedical composition wherein the microbubbles have a diameter of about 1 micron to about 10 microns.

Additional Compounds

In some embodiments, the disclosure provides for one or more compounds wherein A is a carbamate or carbonate group (—$NR^2$—C(O)—O— or —O—C(O)—O—).

In some embodiments, the disclosure provides for one or more compounds wherein A is an amide group (—$NR^2$—C(O)—).

In some embodiments, the disclosure provides for one or more compounds wherein A is a carboxy ester group (—O—C(O)—).

In some embodiments, the disclosure provides for one or more compounds wherein A is a urea group (—$NR^2$—C(O)—$NR^2$—).

In some embodiments, the disclosure provides for one or more compounds wherein A is a guanidinyl group (—$NR^2$—C($NR^2$)—$NR^2$—).

In some embodiments, the disclosure provides for one or more compounds wherein A is a thiourea group (—$NR^2$—C(S)—$NR^2$—).

In some embodiments, the disclosure provides for one or more compounds wherein A is a thioester group (—S—C(O)—).

In some embodiments, the disclosure provides for one or more compounds wherein B is an ethylene glycol group.

In some embodiments, the disclosure provides for one or more compounds wherein B is an polyethylene glycol group wherein the polyethylene glycol is from three (3) to nine (9) units of —$CH_2CH_2$—O—.

In some embodiments, the disclosure provides for one or more compounds wherein X is trimethyl silyl ($Me_3Si$—).

In some embodiments, the disclosure provides for one or more compounds wherein X is tributyl silyl ($Bu_3Si$—).

In some embodiments, the disclosure provides for one or more compounds wherein X is tertbutyldimethyl silyl ($Me_2Bu^tSi$—).

In some embodiments, the disclosure provides for one or more compounds wherein X is phenyldiisopropyl silyl ($PhPr^i_2Si$—).

In some embodiments, the disclosure provides for one or more compounds of Formula Ia wherein the structure is:

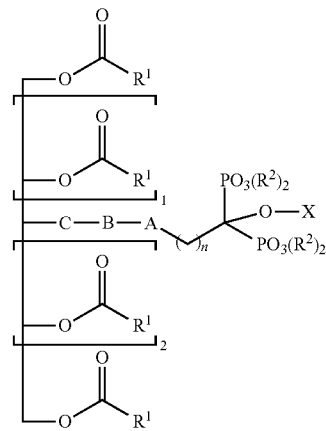

and n is from 3-7.

In some embodiments, the disclosure provides for one or more compounds of Formula Ia wherein the structure is:

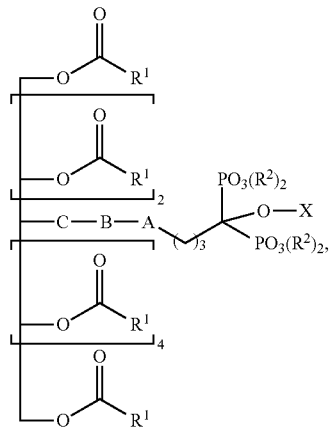

B is —O—($CH_2CH_2$—O)$_n$-E where E is a covalent bond and n is from 3-7, C is

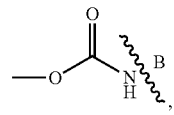

A is a covalent bond, and X is silyl.

In some embodiments, the disclosure provides for one or more compounds of Formula Ia wherein the structure is:

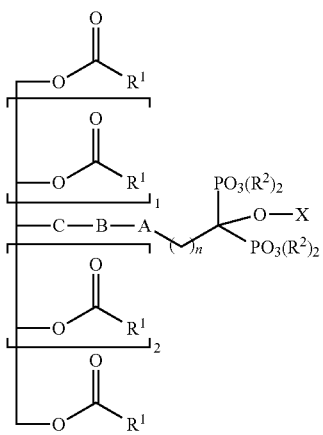

B is —O—(CH$_2$CH$_2$—O)$_n$-E where E is a covalent bond and n is 1, C is

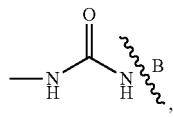

A is a covalent bond, and X is silyl.

In some embodiments, the disclosure provides for one or more compounds of Formula I wherein R$^1$ is a C$_{14}$-C$_{18}$ alkenyl, R$^2$ is a C$_2$ alkyl, A is

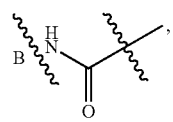

and B is —O—(CH$_2$CH$_2$—O)$_n$-E where E is a covalent bond and n is from 3-7.

In some embodiments, the disclosure provides for one or more compounds of Formula II wherein A is a covalent bond, each n is 1, each R$^2$ is a C$_{14}$-C$_{18}$ alkyl, and X is silyl.

In some embodiments, the disclosure provides for one or more compounds of Formula II wherein A is

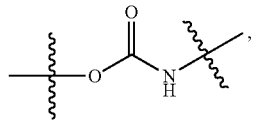

each R$^1$ is a C$_{14}$-C$_{18}$ alkyl, each R$^2$ is a H, and X is H.

In some embodiments, the disclosure provides for one or more compounds of Formula III wherein m is 5.

In some embodiments, the disclosure provides for one or more compounds of Formula III wherein m is 5 and X is silyl.

In some embodiments, the disclosure provides for one or more compounds of Formula III wherein each R$^1$ is a C$_{14}$-C$_{22}$ alkyl, X is hydrogen and m is 3.

In some embodiments, the disclosure provides for one or more compounds of Formula III wherein each R$^1$ is a C$_{14}$-C$_{22}$ alkyl, X is hydrogen and each R$^2$ is H.

In some embodiments, the disclosure provides for one or more compounds of Formula III wherein each R$^1$ is a C$_{14}$-C$_{22}$ alkyl, X is hydrogen and each R$^2$ is a C$_6$ heteroaryl.

In some embodiments, the disclosure provides for one or more compounds of Formula IV wherein X is hydrogen and R$^2$ is a C$_1$-C$_6$ alkyl.

In some embodiments, the disclosure provides for one or more compounds of Formula IV wherein X is substituted sulfonyl and R$^2$ is a C$_{14}$-C$_{22}$ alkyl.

In some embodiments, the disclosure provides for one or more compounds of Formula IV wherein X is hydrogen and R$^2$ is a C$_{14}$-C$_{22}$ alkyl.

In some embodiments, the disclosure provides for one or more compounds of Formula V wherein n is from 3-7.

In some embodiments, the disclosure provides for one or more compounds of Formula V wherein m is from 7-22 and n is from 3-7.

In some embodiments, the disclosure provides for one or more compounds of Formula V wherein m is from 14-22 and n is from 3-7.

In some embodiments, the disclosure provides for one or more compounds of Formula V wherein M is CH$_2$—O, W is O, Z connected to C=W is NH, X is silyl, m is from 16-22 and n is from 3-5.

In some embodiments, the disclosure provides for one or more compounds of Formula V wherein M is CH$_2$—NH, W is NH, Z connected to C=W is NH, X is H, m is from 16-22 and n is from 3-5.

In some embodiments, the disclosure provides for one or more compounds of Formula V wherein M is CH$_2$—O, W is O, Z connected to C=W is O, X is silyl, m is from 16-22 and n is from 3-5.

In some embodiments, the disclosure provides for one or more compounds of Formula V wherein M is CH$_2$—O, W is O, Z connected to C=W is O, X is H, m is from 16-22 and n is from 3-5.

As will be apparent to those skilled in the art, the compounds described herein can be in different forms, including, but not limited to a suspension, a colloid, an emulsion, an aerosol, a sol, a gel, a foam.

Formation of Microbubbles

This disclosure also encompasses methods for preparing a solution of microbubbles.

In some embodiments, the method comprises delivering energy to a solution comprising a bubble-forming material. In some embodiments, the bubble-forming material comprises the fatty-acid glycerol ester derivative compounds described herein. In some embodiments, the bubble-forming material comprises other compounds additional to or in replacement of the fatty-acid glycerol ester derivative compounds described herein.

In some embodiments, the energy provided is sufficient to cause the bubble-forming material to form microbubbles in the solvent. The energy can be provided from ultrasound, mechanical force, or microwave sources.

In some embodiments, the bisphosphonate group of the compounds disclosed herein, in the form of a microbbubble, has an affinity to a calcium-containing material (or other metal target) or other plaques. In various embodiments, the bubble-forming material further comprises a bio-lipid, surfactant, synthetic polymer, or protein. In various embodiments, one or more of these compounds is/are not chemically linked to the bisphosphonate group.

In some embodiments, the targeting bisphosphonate group is disposed exclusively on the exterior surface of the microbubbles. In other embodiments, some or all of the bisphosphonate group is disposed beneath the exterior surface of the microbubbles. It will be appreciated that the location of the bisphosphonate group may be dependent upon environmental conditions such as solvent polarity, pH, ionic strength, etc., and may change with changing conditions.

Where the microbubbles comprise a core containing a fluid having a normal boiling point less than about 30° C. or 35° C., such may comprise air, $CO_2$, a fluorinated $C_{1-6}$ hydrocarbon (e.g., perfluoropropane), or a combination thereof. In some embodiments, the core may comprise a fluid comprising a condensed gas; i.e., the composition is at a temperature below the boiling point of the fluid. For example, pentafluoropentane, with a boiling point of 29.5° C., may exist as a liquid at ambient temperature, but as a gas at physiological temperatures (e.g., 3 7° C.). Such a fluid is considered within the scope of the present disclosure.

The microbubbles of interest include a shell surrounding a core. In some embodiments, the shell is composed of one or more compounds disclosed herein and the shell may include other materials such as bio-lipids, proteins (e.g., albumin), surfactants, biocompatible polymers.

In some embodiments, the core includes an FDA approved therapeutic, an FDA approved diuretic, and/or a pharmaceutically acceptable excipient or any combination thereof. Specific examples of such materials are provided herein. In some embodiments, the hollow core is filled with a gas or low boiling fluid, for example a fluorinated hydrocarbon. Other examples of such gases and fluids are also provided herein. The microbubbles are designed with a shape and size to nucleate cavitation, i.e. the formation and collapse of gaseous bubbles. The violent collapse of cavitation bubbles releases energy that can cause the fragmentation of a plaque or an adjacent mass.

In some embodiments, the microbubbles comprise one of more compounds described herein and one or more pharmaceutically acceptable excipients, or a combination of one or more compounds described herein and one or more bio-lipids, surfactants, synthetic polymers or proteins and one or more pharmaceutically acceptable excipients. In some embodiments, the excipient is sterilized water or sterilized physiological fluid.

In some embodiments, the microbubbles described herein are modified to carry chemical tags on or near their surface. Such tags are selected to target specific locations, masses, or structures either in-vitro or in-vivo. Such tags include, but are limited to, fluorophores, dyes (fluorescein and other such known dyeing compounds), radiolabeled compounds, compounds with FRET activity and the like. Such tags may be covalently bonded onto the bubble forming material. In an embodiment, one or more tags are NOT covalently bonded but rather are bonded thru ionic, Van Der Waals, and/or other such intermolecular forces. In an embodiment, one or more tags are NOT bonded, but rather aggregate or self-assemble on to the microbbubble surface. Because of this targeting moiety/methodology, the microbubbles concentrate at a centralized location, plaque, mass, and/or structure and can be used in therapeutic treatments as described herein.

Alternatively or additionally, the microbubbles can be used to transport a load of material within the core to a specific mass, location, or structure in-vitro or in-vivo. Disruption of the microbubbles in certain environments leads to delivery of the payload in the core. Such delivery can be pre-engineered into the constitution of the microbubble composition.

In some embodiments, microbubbles are suitable for medicinal applications and they are prepared by adapting a process for creating hollow spheres for use in paints and surface treatments (C. J. McDonald and M. J. Devon, Advanced in Colloid and Interface Science, 2002, 99, 181-213; herein incorporated in its entirety).

In some embodiments, microbubbles (including multi-layered microbubbles) are prepared using methods known in the art; for example, according to the process reported in Liu et al., J. Controlled Release, 114 (2006) 89-99, and references cited therein. In some embodiments, microbubbles are prepared according to the process reported in Hu et al., J. Controlled Release, 147 (2010) 154-162, and references cited therein. In some embodiments, microbubbles are prepared according to the process reported in Hernot et al., Adv. Drug Delivery Rev. 60 (2008) 1153-1166, and references cited therein. In some embodiments, microbubbles are prepared according to the process reported in Geers et al., J. Controlled Release 148 (2010) e57-e73 (abstracts), and references cited therein. In some embodiments, microbubbles are prepared according to the process reported in Tinkov et al., J. Controlled Release 143 (2010) 143-150, and reference cited therein. Additional synthetic details for preparing (untagged) microbubbles can be found in Mayer et al., Adv. Drug Delivery Rev. 60 (2008) 1177-1192. The procedures from any of the above-cited references can be modified according to the examples provided herein below so as to prepare the targeting microbubbles of interest. Each reference cited herein is incorporated in their entirety.

In some embodiments, the individual compounds of the bubble-forming material are chemically bonded to each other via covalent bonds, ionic bonds, hydrogen bonds, or a combination thereof. In some embodiments, two or more of the various compounds are separate molecules (not chemically bonded) but are associated with each other as part of the same microbubble. For example, the "anchoring moiety" may be a separate compound from the "targeting moiety," and both compounds together form microbubbles. Accordingly, it is contemplated that even three, four, or even five separate molecules can act in a cooperative manner to for a microbubble.

For example, gas-filled microbubbles are synthesized with one or more tags for targeting a specific tissue, tumor, mass, stone or bone. The bubbles are delivered to the target as part of a pharmaceutically acceptable formulation. Upon attachment to or association with the target, cavitation is induced with consequent disruption or fragmentation of the target.

The contents of the bubble can vary with application. In some embodiments, the bubble contains air, $CO_2$, one or more fluorinated gases (e.g. a fluorinated alkane such as perfluoropropane or perfluoropentane), another gas, or mixtures thereof. In other embodiments, the bubble may contain a low boiling (e.g., normal boiling point less than about 30° or 35° C.). This allows that a deflated bubble may be injected into the subject, said bubble inflating as it heats to physiological temperatures (ca. 37° C.). In other embodiments, the bubbles can be filled partially or completely with a payload other than a gas, such as a pharmaceutically active agent, a cytotoxic agent, an imaging agent, or the like.

The bubbles are intended for delivery to the site of a targeted mass or tissue that is to be reduced in size or eliminated. The bubbles are tagged with a targeting moiety so that they selectively bind or associate with the target.

Various sizes and shapes of bubbles are suitable based on the specific intended applications. In some embodiments, the microbubbles are selected from spherical, ellipsoidal, disk-shaped, and asymmetric shapes. In some embodiments, the shape of the bubbles is not static. For example, in some embodiments, the unperturbed bubbles may be spherical, but the bubbles may adopt a different shape such as ellipsoidal or disk-shaped when an external force (e.g., a flowing fluid such as blood) is present.

In some embodiments, the microbubbles have an average diameter (wherein "average diameter" refers to the largest dimension for non-spheroidal shapes) between 0.1 µm and 10 µm, or between 0.5 µm and 10 µm, or between 1 µm and 10 µm. In some embodiments, the average diameter is between 0.5 µm and 3 µm, or between 1 µm and 2 µm. In some embodiments, the microbubbles have an average diameter less than 10 µm, or less than 5 µm, or less than 1 µm, or less than 0.5 µm, or less than 0.1 µm. In some embodiments, the microbubbles have an average diameter greater than 0.1 µm, or greater than 0.5 µm, or greater than 1 µm, or greater than 5 µm, or greater than 10 µm. The synthetic processes described herein allow the production of bubbles of various sizes and materials. It will be appreciated that use of the term "microbubbles" is not intended to limit the size of the bubbles to any particular range (e.g., micron diameters).

In some embodiments, the microbubbles are targeted to the mass of interest by the attachment of a targeting agent or tag, for example to the surface of the bubble. For example, microbubbles can be chemically functionalized using a variety of techniques, the details of such techniques being dependent on the exact chemical moiety to be attached.

Examples of methods of attachment of the targeting moieties include covalent and ionic bonds. The targeting moiety is chosen based on properties of the target tissue or mass as well as the structure and chemical properties of the microbubbles. A variety of targeting moieties may be used, some of which are described in more detail below.

Targeting moieties and other functional groups can be attached asymmetrically or in patterns as needed for a particular application. In some embodiments, there is directional modification of the surface of the bubbles. For some applications, only one part of the surface of the microbubble is functionalized with a tagging moiety in order to direct energy toward or away from the intended target.

Methods of Synthesizing Compounds

Embodiments of the present disclosure also provide methods for synthesizing the fatty-acid glycerol ester derivative compounds.

The compounds of the present technology can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of the present technology contain one or more chiral centers, such compounds can be prepared or isolated as pure stereoisomers, i.e., as individual enantiomers or d(1) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Gem-Phosphonates

In one general embodiment, the method of synthesizing fatty-acid glycerol ester derivatives involves synthesizing the desired gem-phosphonate group. This procedure is well within the grasp of the skilled artisan and one will appreciate that modifications to the reaction conditions or the use of other synthetic methodology to put the phosphorus groups on can be done without a burden, especially if such modification are needed to accommodate differing sorts of organic functionalities away from the gem-phosphonate center (i.e. accommodating for orthogonal functional group chemistry).

In a general embodiment, the method involves reacting an electrophilic functional group (for eventual placement on the fatty-acid glycerol ester derivative) with a nucleophilic organophosphorus reagent. This is reactivity is usual however, the skilled artisan, depending on the exact reaction chosen, may alter the reactivity and make the organophosphorus reagent the electrophile. Such modifications are well within the purview of the skilled artisan in organic synthesis. That said, electrophilic functional groups readily susceptible to an organophosphorus nucleophile include, but are not limited to, ketones, aldehydes, and In a general embodiment, the method of synthesizing gem-phosphonate derivatives comprises the synthesis according to Scheme 1a.

Scheme 1a.

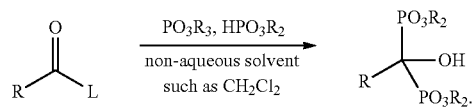

Of course, one skilled in the art can elaborate the hydroxyl functionality to put on further functional groups, such as a silyl functional group. These types of reactions are very straightforward and usually involve just a simple substitution reaction with the hydroxyl group (or hydroxyl anion made in-situ) being the nucleophile and reacting with an electrophilic organic functional group (for example in the case of the silyl functionality, the electrophile might be chloro-tributylsilane).

As described in Scheme 1, L is a leaving group suitable to make a compound which is reactive to an amine. The leaving group will be displaced by the nitrogen atom of the amine. Such reactions are well-known in the art and it is readily recognized that the activated intermediate may not need to be isolated. Further, R is recognized as any organic functional group so long as the reactions conditions do not degrade or otherwise alter the course of the reaction so as to produce an undesired product compound.

Carbamates

In one general embodiment, the method of synthesizing fatty-acid glycerol ester carbamate derivatives involves reacting an appropriately O-protected/O-unprotected fatty-acid glycerol ester derivative with a coupling reagent. Such coupling reagents are known in the art and exemplary coupling reagents include phosgene, 1'-carbonyldiimidazole (CDI), haloformates, and the like. These coupling reagents are generally electrophilic and the un-protected oxygen atom on the derivative is the nucleophile. Such reactions are usually conducted under basic conditions, though Lewis acidic conditions can also be employed. In some embodiments, Lewis acid is trimethylsilyl bromide. This reaction produces a first, activated intermediate which then will lead to the carbamate product either in a one-step, two-step procedure or by consecutive synthetic transformations with the isolation (optionally in a scalemic workup) of the first intermediate followed by a reaction with an amine nucleophile.

In a general embodiment, the method of synthesizing fatty-acid glycerol ester derivatives comprises the synthesis according to Scheme 2a.

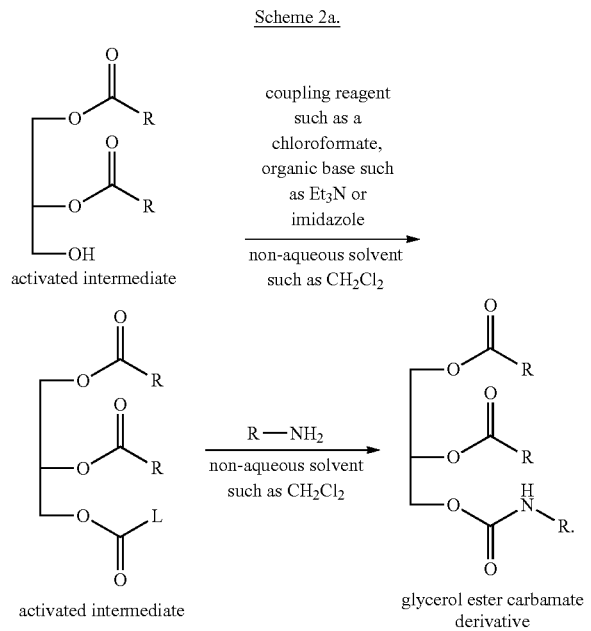

Scheme 2a.

As described in Scheme 2a, L is a leaving group suitable to make a compound which is reactive to an amine. The leaving group will be displaced by the nitrogen atom of the amine. Such reactions are well-known in the art and it is readily recognized that the activated intermediate may not need to be isolated. Further, R is recognized as any organic functional group so long as the reactions conditions do not degrade or otherwise alter the course of the reaction so as to produce an undesired product compound.

Of course, the skilled artisan will recognize that carbonyl coupling reactions are only one way of making a carbamate compound and that synthetic variations are easily designed. Such variations may include reactions involving the Curtius Rearrangement, copper catalyzed organoindium three component coupling of aldimines and acid chlorides, zirconium catalyzed dialkyl carbonate exchange with amines, nickel catalyzed reduction of nitriles and the like.

Carbonates

In one general embodiment, the method of synthesizing fatty-acid glycerol ester carbonate derivatives involves a synthetic methodology similar to the carbamate methodology described above. In general, the methodology involves reacting an appropriately O-protected/O-unprotected fatty-acid glycerol ester derivative with a coupling reagent. Such coupling reagents are known in the art and exemplary coupling reagents include phosgene, 1'-carbonyldiimidazole (CDI), haloformates, and the like. For carbonates, chloroformates are especially advantageous as they are often commercially available, provide excellent reactivity to the hydroxyl group of the fatty-acid glycerol derivative, and provide the carbonate product directly.

In a general embodiment, the method of synthesizing fatty-acid glycerol ester carbonate derivatives comprises the synthesis according to Scheme 3a.

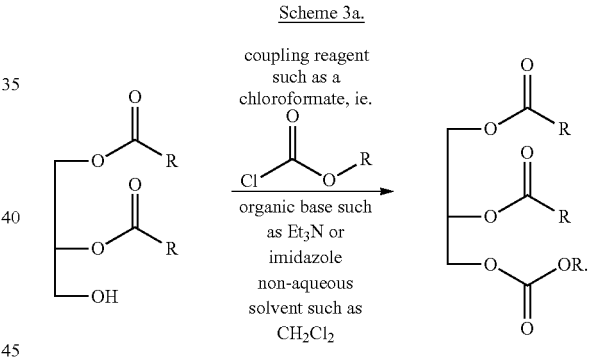

Scheme 3a.

As described in Scheme 3a, R is recognized as any organic functional group so long as the reactions conditions do not degrade or otherwise alter the course of the reaction so as to produce an undesired product compound.

Other Carbonyl Containing Groups

The compounds of the present disclosure not only cover carbamate and carbonate linkages on the fatty-acid glycerol ester derivative but also functional groups encompassing a general set of carbonyl-containing and carbonyl-like groups designated C. Linkage to these C group corresponds to the hydroxyl functional group on the other fatty-acid glycerol ester carbonate and carbamate derivatives.

These C groups include:

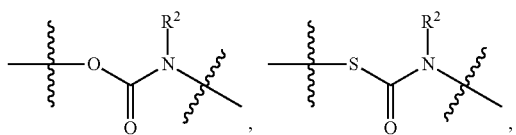

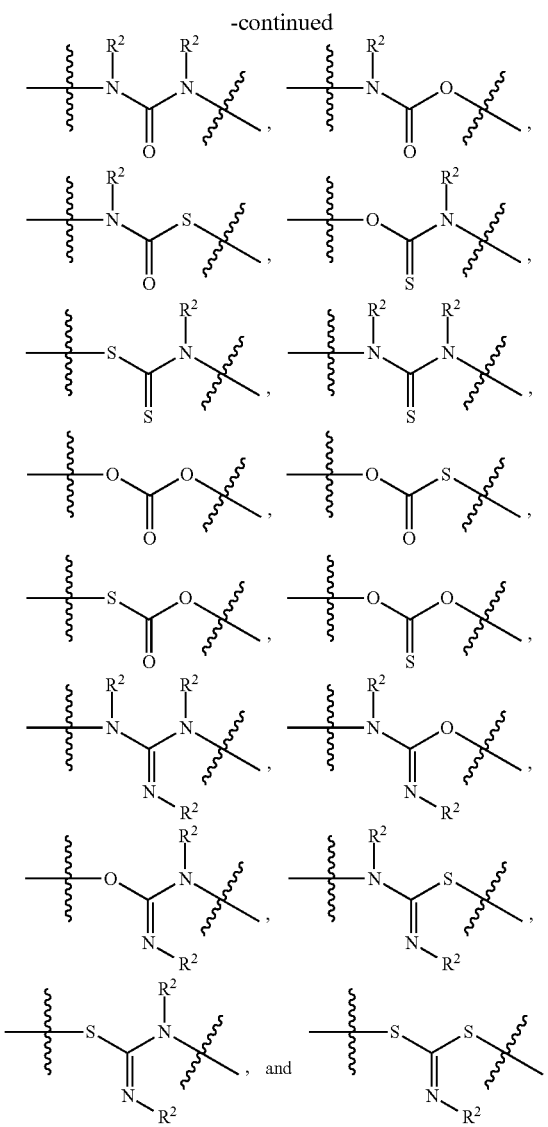

It is appreciated that appropriately O-protected fatty acid ester derivative can have an unprotected hydroxyl group at the end of the glycerol chain or in the middle of the glycerol chain. These hydroxyl functional groups can be transformed into amino- or sulfo-groups by a number of known methodologies. Such rudimentary functional group transformations are well known in the art and often involve simple substitution ($SN_1$ or $SN_2$) reactions where the hydroxyl group has been transformed into an electrophilic group, such as a sulfonate ester (i.e. a tosylate group). Then, an amino- or sulfo-nucleophile is reacted with the electrophile and the oxygen-containing group is displaced.

It is acknowledges that some of these carbonyl-containing and carbonyl-like groups may not be thermally nor hydrolytically stable and thus, low temperature (as low as −78° C.) storage/formation conditions may be required for these derivatives. Of course, such techniques for stabilizing and/or synthesizing these compounds are within the grasp of the skilled artisan.

In a general embodiment, the method of synthesizing these fatty-acid glycerol ester carbonyl-containing and carbonyl-like derivatives include the methodologies described for the carbonate and carbamate derivatives. Further, modifications to these procedures to arrive at a carbonyl-like derivative containing different heteroatoms are known in the art and within the grasp of the skilled artisan. For example, carbonyl-like derivatives like urea and mixed thio-ureas can be made from modifications such as reacting an appropriately O-protected-amino functionalized glycerol fatty acid with S,S-dimethyl dithiocarbonate to forma mixed thio-derivatized carbonyl-like derivative; or reacting said amine with carbon monoxide in DMF to form the thiourea derivative, and then optionally, reacting that product oxygen gas to form the urea derivative (T. Mizuno, T. Nakai, M. Mihara, Synthesis, 2009, 2492-2496, which is herein incorporated in its entirety).

Of course, there are many combination of the heteroatoms O, N, and S which can be inserted into the linkage. That said the skilled artisan can utilize an appropriate organic synthesis textbook to choose the appropriate reaction and conditions under which to make these compounds, even if sometimes modifications such as adding Lewis-acid catalysts or adding organic bases (perhaps creating heteroatom anions) such as tert-butyl lithium are called for. Such modifications are within the training of an artisan skilled in organic synthesis. Dr. Douglass F. Taber, professor at the University of Delaware, has a website containing information on general ideas, tips and references on how to make these carbonyl-like derivatives. Dr. Taber's website is freely accessible at: http://www.organic-chemistry.org as of Jun. 20, 2016.

One skilled in the art will recognize that the same modifications to make these carbonyl-like derivatives is used to make the carbonyl-like derivatives that are included in compounds of the present disclosure having groups designated B. Some the groups in B are inclusive in the list of C. Some groups of B possess only one heteroatom flanking the double bond in the carbonyl-like group. Such groups include (but are not limited to) amides, esters, thioesters, and thioamides. These groups are also made by the same chemistries described herein where the skilled artisan must cobble the carbonyl-like group together from a choice of O, N, and S in such positions.

In an embodiment, the disclosure provides methods for synthesizing the compounds comprising the steps of:
1) contacting a compound having the structure:

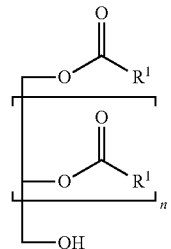

with a carboxy coupling reagent (CCR) under basic conditions to produce an activated intermediate;
2) optionally isolating the activated intermediate;
3) contacting the activated intermediate with an amine having the structure:

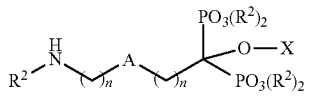

to produce a carbamate intermediate having the structure of

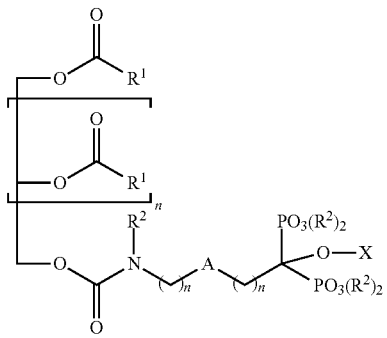

wherein:
each n is independently selected from 1-7;
each $R^1$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl;
each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;
X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;
A is present or optionally absent and when present is selected from the group consisting of: acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester, wherein any of these functional groups listed for A may be covalently bonded on either side to either one of the

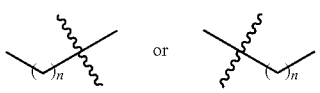

moieties;
or a tautomer and/or a pharmaceutically acceptable salt thereof.
In some embodiments, the carboxy coupling reagent is para-nitro-phenylchloroformate (PNPCl). In some embodiments, the carboxy coupling reagent is 1'-Carbonyldiimidazole (CDI).

In another embodiment, the method further comprises the steps of
4) contacting the carbamate intermediate with a Lewis acid under non-aqueous conditions; and
5) adding a protic acid.
In other embodiments, the disclosure provides methods for synthesizing the compounds comprising the steps of
1) contacting a glycerol ester compound having the structure:

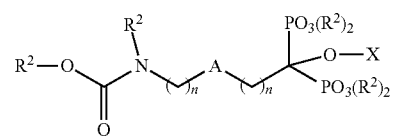

with a Lewis acid under non-aqueous conditions; and
2) adding a protic acid to produce a gem-phosphonate compound having the structure:

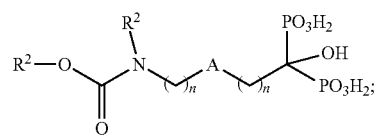

wherein $R^2$, n, A and X are set out in the embodiment above.
In some embodiments, the Lewis acid is trimethylsilyl bromide and the protic acid is methanol.
In some embodiments, the disclosure provides for a method wherein the Lewis acid is trimethylsilyl bromide; and the protic acid is methanol.
In some embodiments, the disclosure provides for a method wherein the carboxy coupling reagent is para-nitro-phenylchloroformate (PNPCl).
In some embodiments, the disclosure provides for a method wherein the carboxy coupling reagent is 1'-Carbonyldiimidazole (CDI).
In some embodiments, the disclosure provides for a method wherein the activated intermediate is not isolated.
In some embodiments, the disclosure provides for a method wherein the synthetic steps comprise the following synthetic scheme:

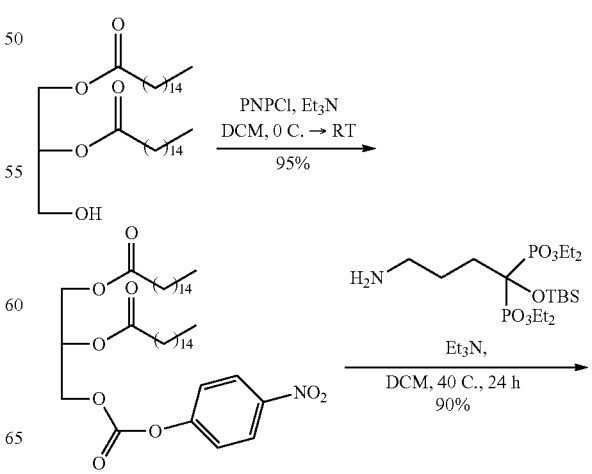

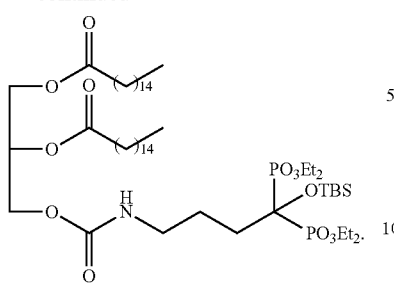

In some embodiments, the disclosure provides for a method wherein the synthetic steps comprise the following synthetic scheme:

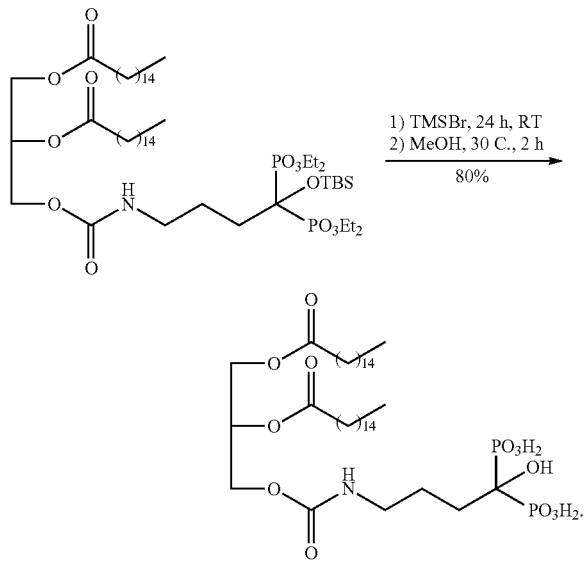

In some embodiments, the disclosure provides for a method of synthesizing a gem-phosphonate compound, the method comprising the following synthetic scheme:

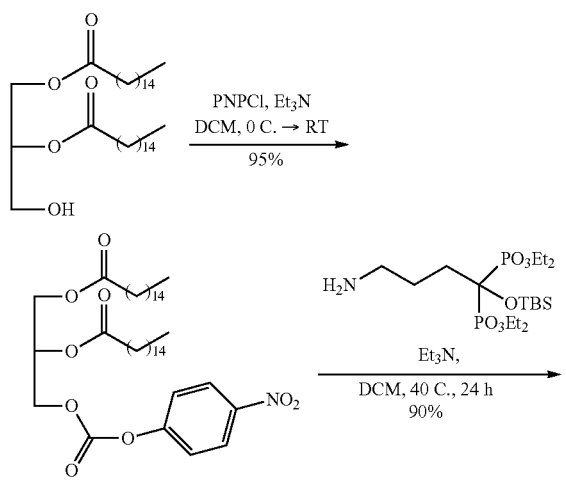

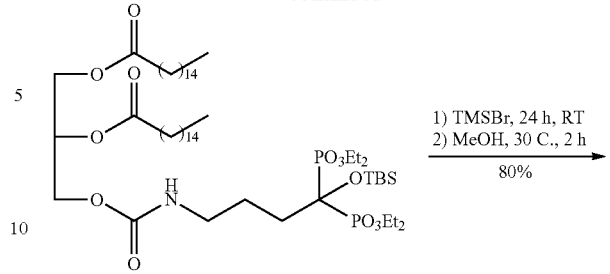

In some embodiments, the disclosure provides for a method for preparing microbubbles, the method comprising delivering a sufficient amount of energy to one or more compounds described herein to cause the formation of microbubbles.

In some embodiments, the disclosure provides for a method wherein the energy is provided by ultrasound, mechanical force, or microwaves.

In some embodiments, the disclosure provides for a method for binding a physiological plaque, the method comprising delivering an effective amount of a pharmaceutical composition described herein comprising microbubbles to a subject in need thereof.

In some embodiments, the disclosure provides for a method further comprising applying energy to the microbubbles, wherein the energy in the form of electromagnetic or ultrasound energy and is sufficient to cause cavitation of the microbubbles, and wherein the cavitation releases sufficient energy to cause destruction of cell, tissue, or calcium-containing mass at the site within the subject.

Herein it is understood that amino, keto, thio, hydroxyl, and any other necessary protecting groups and their methods of deprotection are known in the art, such as those described in T. W. Greene and P. G. M. Wuts, Protecting Groups in Organic Synthesis, Third Edition, Wiley, New York, 1999 (the disclosure of which is incorporated by reference for all purposes).

A skilled artisan will further recognize that there are additional synthetic functional group modifications that one can use to synthesize microbubble-forming compounds described herein from glycerol derivative intermediates.

Methods of Treatment

The compounds represented by Formula I-V or their tautomers and/or pharmaceutically acceptable salts thereof can effectively act to bind to plaque in the human body and thus treat conditions affected at least in part by the blockage or by physiological plaque buildup in certain tissues. The compounds represented by Formula I-V or their tautomers and/or pharmaceutically acceptable salts thereof have been shown to bind to kidney stones. These compounds can be used to treat conditions or symptoms affected at least in part by blockage due to kidney stones.

In one aspect, the present technology provides for methods of treating a blockage due to plaque in a subject, the method comprising administering one or more compounds of Formula I-V and one or more pharmaceutically acceptable excipients.

In another aspect, the present technology provides for methods of treating a blockage due to plaque in a subject, the method comprising administering one or more compounds of Formula I-V, one or more FDA approved therapeutics, and one or more pharmaceutically acceptable excipients.

In another aspect, the present technology provides for methods of treating a blockage due to plaque in a subject, the method comprising administering one or more compounds of Formula I-V and one or more pharmaceutically acceptable excipients.

In another aspect, the method of treating a blockage due to plaque comprises administration of a pharmaceutical composition to the subject.

In another aspect, the method comprises administration of a pharmaceutical or biomedical composition that comprises microbubbles which themselves comprise one or more compounds of Formula I-V, and optionally, one or more pharmaceutically acceptable excipients.

In another aspect, the microbubbles comprise one or more compounds of Formula I-V and one or more fluorinated hydrocarbons.

In another aspect, the microbubbles comprise one or more compounds of Formula I-V, one or more FDA approved therapeutics, and one or more fluorinated hydrocarbons.

In another aspect, the plaque is a kidney stone.

In another aspect, the plaque is a biliary stone.

In another aspect, the plaque is an atheromatous plaque.

In another aspect, the present technology provides methods for treating a condition or symptom due to plaque in a subject with an effective amount of one or more compounds of Formula I-V as provided herein and a fluorinated hydrocarbon.

In another aspect, the present technology provides methods for treating a condition or symptom due to kidney stones in a subject with an effective amount of one or more compounds of Formula I-V as provided herein and a fluorinated hydrocarbon.

In another aspect, the present technology is directed to methods for treating a disease or condition affected at least in part by kidney stones.

In one aspect, the present technology is directed to methods for binding kidney stones, the method comprises contacting cells (including neurons/microglia/invading macrophages) with an effective amount of one or more compound of Formula I-V as described herein.

In one aspect, the present technology is directed to methods for binding kidney stones wherein the method comprises contacting cells with an effective amount of one or more compounds of Formula I-V. In one aspect, the method for binding kidney stones is performed in-vitro or in-vivo.

In one aspect, the present technology is directed to methods for preparing microbubbles, the method comprising delivering a sufficient amount of energy to one or more compounds to cause the formation of microbubbles.

In one aspect, the present technology is directed to methods for preparing microbubbles, wherein the energy is provided by ultrasound, mechanical force, or microwaves.

In one aspect, the present technology is directed to methods for binding a physiological plaque, the method comprising delivering an effective amount of a pharmaceutical or biomedical composition of any one comprising microbubbles to a subject in need thereof.

In one aspect, the present technology is directed to methods for binding a physiological plaque, the method further comprising applying energy to the microbubbles, wherein the energy in the form of electromagnetic or ultrasound energy and is sufficient to cause cavitation of the microbubbles, and wherein the cavitation releases sufficient energy to cause destruction of a cell, a tissue, or a calcium-containing mass at a site within the subject.

Selective Binding

In another aspect, a method is provided for selectively binding calcium in the presence of other plaques and/or cations. The method includes contacting cells (including neurons/microglia/invading macrophages) with an effective amount of one or more compounds of Formula I-V described herein.

In another aspect, a method is provided for prophylactic therapy or treatment of a subject having a condition or symptom affected at least in part by plaque (or kidney stones), the method comprising administering an effective amount of one or more compounds of Formula I-V or a pharmaceutical composition comprising one or more compounds of Formula I-V to the subject in need thereof.

In an embodiment, the selective binding of calcium is in the presence of potassium cations.

In an embodiment, the selective binding of calcium is in the presence of magnesium cations.

In an embodiment, the selective binding of calcium is in the presence of sodium cations.

In an embodiment, the selective binding of calcium is in the presence of iron cations.

In an embodiment, the selective binding of calcium is in the presence of iron cations.

In an embodiment, the selective binding of calcium is in the presence of iron complexes.

In some embodiments, the present technology provides methods for treating a condition in a subject affected by plaque in either a therapeutic or prophylactic setting. The methods comprise administering of one or more compounds of Formula I-V or a pharmaceutical composition comprising one or more compounds of Formula I-V to a subject in need thereof.

In another aspect, the present technology provides a method wherein one or more compounds of Formula I-V may be administered with one or more other plaque binding compounds, compositions, and/or agents.

The compounds of the present technology are useful in the diagnosis of a diseases or conditions affected by plaque, such as coronary heart disease. In such an embodiment, the detection of the compounds of Formula I-V or the detection of the fluorinated hydrocarbon or the detection of an FDA approved therapeutic in the composition allows for a qualitative and/or quantitative measurement of the plaque or blockage. Accordingly, In an embodiment, the present technology provides for kits, including contrasting agents, dyes, etc., methods of administration, methods of treatment (using the detection information) for clinical or medical therapy.

Compounds of the present technology are shown to have improved safety and potency, such as the potency of binding kidney stones at low concentrations and possessing low relative cytotoxicity. In general, compounds of the present technology are shown to have potency, ameliorate, and/or possess efficacy in treating conditions or symptoms which include, as a component, some affect due to blockage from a plaque, including kidney stones and other blockages from materials; e.g. such those blockages which occur in the lymphatic system.

The amount of active compound administered will vary depending upon the disease treated, the mammalian species, and the particular mode of administration, etc. Suitable doses for the compounds of the present technology can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration. It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

Additional embodiments provide methods of treating a blockage in a subject. In some embodiments, the method comprises applying energy to microbubbles disposed within the subject.

In some embodiments, the microbubbles comprise a targeting moiety with a specific affinity to a target within the subject. In some embodiments, the energy provided to the bubble forming material is effective to cause cavitation of the microbubbles.

In certain embodiments, the methods further comprise administering the microbubble composition to the subject prior to applying the energy. For example, the microbubble composition is administered via injection, inhalation, or implantation.

In some of embodiments, the target is selected from the group consisting of: a calcium-containing mass, a cancerous cell, a tumor, and a tissue.

In some embodiments the target is a calcium-containing mass and the cavitation causes damage to the target.

In other embodiments, the target is a cancerous cell and the cavitation causes lysis of the target cell.

In still other embodiments, the target is selected from the group consisting of: a renal or urinary stone, biliary stone, blood clot, fibroid, cancerous tumor, or atheromatous or other plaque. In some of these embodiments, the cavitation causes damage to the target. Also, some of these embodiments, the microbubbles further comprise a bio-lipid, synthetic polymer, protein, or surfactant.

In other embodiments, the microbubble forming compound(s) lack a targeting moiety.

Still other embodiments include methods of treating blockage in a subject, the method comprising: (a) delivering a solution comprising microbubbles to a site within the subject; and (b) applying energy to the microbubbles.

In some embodiments, the method provides a sufficient amount of energy from electromagnetic or ultrasound sources.

In some embodiments, the method provides a sufficient amount of energy to cause cavitation of the microbubbles.

In some embodiments, the cavitation releases sufficient energy to cause destruction (e.g., lysis or fracture) of the target cell, tissue, tumor, or calcium-containing or other mass within a subject—e.g., to the target renal or urinary stones, biliary stones, blood clots, fibroids, cancerous tumors, and atheromatous plaques.

In certain related embodiments, the microbubbles do not contain a targeting moiety. In these embodiments, the composition comprising one or more compounds described herein is delivered by implantation, inhalation, injection, or by catheter. Where by inhalation or injection, it is envisioned that a microbubble composition has an affinity for a cell, tissue, or calcium-containing mass within the subject.

Various microbubble products are available commercially, including microbubbles marketed under the trade names ALBUNEX®, DEFINITY®, and OPTISON®. In some embodiments, the microbubbles used in the procedures described herein are selected from such commercially available materials and are further modified to include targeting moieties as described herein. In some embodiments, such commercially available materials are mixed with compounds disclosed herein to form various microbubble products.

As an example for illustrative purposes, in one embodiment, microbubbles are prepared in a pharmaceutical composition with one or more of the compounds disclosed herein that are suitable for binding to kidney stones. The microbubbles are administered to a subject suffering from kidney stones. Ultrasound is applied to cause the microbubbles to cavitate and break apart the kidney stones into smaller particles. The smaller particles pass through the kidney/ureter naturally and with limited or no discomfort to the subject.

In an embodiment, the manufactured bubbles are specifically delivered to the surface or an area adjacent or in the immediate vicinity of the targeted tissue or mass.

Alternatively, microbubbles that contain targeting gem-phosphonate groups allow for the compound(s) to concentrate on or near the surface of the targeted tissue or mass. Energy from external sources (e.g. ultrasound, RF energy, or the like) is then applied in order to induce cavitation. The engineered bubbles act as a cavitation nucleus upon interaction with ultrasound or by absorption of radio frequency energy causing local heating and cavitation. Expansion of bubbles and their rapid collapse causes a shock wave that can fragment or lyse the targeted mass or plaque. In some embodiments, electromagnetic (EM) energy of frequencies between 400 kHz and 10 MHz is suitable because it propagates through tissue without strong interactions (due to low electrical conductivity). In an example, standard ultrasound units are applied within or adjacent to the body with sufficient power to initiate cavitation of the pre-positioned bubbles. For certain masses, the release of energy will cause fragmentation, as in the case of kidney stones. For other conditions, the energy release will cause the lysis of cells, as in tumors.

Microbubble Delivery and Administration

Delivery into or near the targeted mass, tissue, tumor, stone, bone or other site of interest can be achieved by a variety of means and as is appropriate for the application.

Microbubble compositions may be administered, for examples, by injection or spray. The specific composition of microbubbles can vary depending on specific formulations or preparations using surfactants or other additives for dispersal.

In some embodiments, microbubble compositions are administered to the blood, bile, urine, or cerebral spinal fluid. In some embodiments, microbubble compositions are administered into organs by percutaneous injection. In some embodiments, microbubble compositions are administered via an orifice of the body. Orifices include any opening such as the mouth, nose, eyes, vagina, urethra, and ears. In some embodiments, microbubble compositions are administered under the skin (subcutaneous administration).

In some embodiments, microbubble compositions are administered directly at the target site, such as by direct implantation into a target tissue or mass. In some such cases, it is not necessary for the microbubble compositions to be manufactured with targeting agents.

In other embodiments, microbubble compositions are administration at a remote location (e.g., into the bloodstream via percutaneous injection) and are allowed to concentrate at the targeted site.

Administration and Pharmaceutical Compositions

The present technology provides novel compounds possessing kidney stones binding activity and, accordingly, are useful in treating conditions and/or disorders affected by (or at least in part by) physiological plaque and/or kidney stones.

Methods for treatment of chronic diseases affected by physiological plaque and/or kidney stones are also encompassed by the present disclosure. Said methods of the disclosure include administering a therapeutically effective amount of a pharmaceutical or biomedical composition of any one or more compounds of Formula I-V and optionally in combination with one or more FDA approved therapeutics or one or more FDA approved diuretics. The compounds and solvates of the disclosure can be formulated in pharmaceutical compositions. These compositions can comprise a pharmaceutically acceptable excipient, carrier, buffer, stabilizer or other materials well known to those skilled in the art. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In other embodiments, it will be appreciated that the microbubble compositions are introduced as part of a pharmaceutical formulation which may include, for example, solvents or other carriers, additives (e.g., stabilizers and preservatives, colorants, surfactants, pH-modifiers, etc.), and/or one or more pharmaceutically active agents.

Microbubble compositions can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In general, the one or more compounds of the microbubbles disclosed herein will be administered in a therapeutically effective amount. The actual amount of the one or more compound of the present technology, i.e., the active ingredients, will depend upon numerous factors such as the severity of the disease to be treated, the age and relative health of the subject, the potency of the compound used, the route and form of administration, and other factors well known to the skilled artisan.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In an embodiment, the pharmaceutical composition for administration comprises microbubbles formed from one or more of the compounds of Formula I-V.

A composition can be administered alone or in combination with other treatments, either simultaneously or sequentially dependent upon the condition to be treated.

In general, the compounds of the present technology will be administered in a therapeutically effective amount by any of the accepted modes of administration for agents that serve similar utilities. The actual amount of the compound of the present technology, i.e., the active ingredient, will depend upon numerous factors such as the severity of the disease to be treated, the age and relative health of the subject, the potency of the compound used, the route and form of administration, and other factors well known to the skilled artisan. The compounds can be administered at least once a day, preferably once or twice a day.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the present technology, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the compound(s) may not be related to plasma concentration.

The amount of agent or composition administered may be dependent on a variety of factors, including the sex, age, and weight of the subject being treated, the severity of the affliction, the manner of administration, and the judgment of the prescribing physician.

The compositions are comprised of in general, a compound of the present technology in combination with at least one pharmaceutically acceptable excipient. Acceptable excipients are non-toxic, aid administration, and do not adversely affect therapeutic benefit of the claimed compounds. Such excipient may be any solid, liquid, semisolid or, in the case of an aerosol composition, gaseous excipient that is generally available to one of skill in the art.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the present technology formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt. %) basis, from about 0.01 99.99 wt. % of a compound of the present technology based on the total formulation, with the balance being one or more suitable pharmaceutical excipients.

Preferably, the compound is present at a level of about 1 80 wt. %. Representative pharmaceutical formulations are described below.

FORMULATION EXAMPLES

The following are representative pharmaceutical formulations containing a compound of Formula I-V.

Formulation Example 1—Tablet formulation

The following ingredients are mixed intimately and pressed into single scored tablets.

| Ingredient | Quantity per tablet, mg |
| --- | --- |
| compound of this the present technology | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
| --- | --- |
| compound of this the present technology | 200 |
| lactose, spray-dried | 148 |
| magnesium stearate | 2 |

Formulation Example 3—Suspension Formulation

The following ingredients are mixed to form a suspension for oral administration.

| Ingredient | Amount |
| --- | --- |
| compound of this the present technology | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
| --- | --- |
| compound of this the present technology | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
|---|---|
| Compound of the present technology | 500 mg |
| Witepsol ® H-15 | balance |

The following synthetic and biological examples are offered to illustrate the present technology and are not to be construed in any way as limiting the scope of this the present technology.

EXAMPLES

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992), and Organic Reactions, Volumes 1-40 (John Wiley, and Sons, 1991).

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992), and Organic Reactions, Volumes 1-40 (John Wiley, and Sons, 1991).

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-triazolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimoles
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
TLC=thin layer chromatography
UV=ultraviolet
wt. %=weight percent
μM=micromolar The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

Example 1: Synthesis of Amino-Bisphosphonate Compounds

Shown below are organic syntheses that are representative of the general synthetic methodology used to make the gem-phosphonate compounds of the present disclosure. Of course, one skilled in the art could use other commercially available starting materials and reagents in order to arrive at one or more synthetic intermediates in this procedure.

4-chlorobutyryl chloride
(CAS 4635-59-0)

chloro-bisphosphonate
(CAS 890848-00-7)

azido-bisphosphonate
(CAS 890848-01-8)

amino-bisphosphonate
(CAS 90848-02-9)

Lab Supplies
Reagents (to Make Ca. 10 g of Amino-Bisphosphonate)
 4-Chlorobutyrylchloride (Aldrich C30604, 100 g bottle but will only use 30 g)
 Triethylphosphite (Aldrich T61204, 100 mL bottle but will only use 40 mL)
 Dichloromethane, anhydrous (Aldrich 270997, 1 L bottle but will only use 800 mL)
 Diethylphosphite (Aldrich D99234, 250 g bottle but will only use 30 g)
 Dimethylaminopyridine (Aldrich 39405, 250 g bottle but will only use 30 g)
 Tert-butyldimethylsilylchloride (Aldrich 190500, 100 g bottle but will only use 35 g)
 Sodium azide (Aldrich S2002, 25 g bottle but will only use 13 g)
 Dimethylformamide, anhydrous (227056, 1 L bottle but will only use 500 mL)
 Palladium on Carbon, 10 weight % (Aldrich 205699, 10 g bottle but will only use 2.5 g)
 Absolute ethanol, 200 proof (Aldrich 459844, 1 L bottle)
Additional Lab Supplies and Materials
 Dichloromethane
 Distilled water
 1M solution of hydrochloric acid (aqueous)
 Saturated solution of sodium chloride (aqueous)
 Saturated solution of lithium chloride (aqueous)
 Sodium sulphate
 Celite
 Silica gel
 Argon gas
 Hydrogen gas
 Deuterated chloroform
Procedure The amino-bisphosphonate is a known compound, and was synthesized according to a procedure outlined in the chemical literature (*J. Med. Chem.* 2006, 49, 3060-3063). The major bottleneck in this procedure is the first step, in which the intermediate chloro-bisphosphonate is synthesized from 4-chlorobutyrylchloride. This step not only produces low yield of product (15-40%), but purification is also challenging due to the presence of excess starting materials as well as many additional unidentified by-products. However, this procedure remains the best that was found in the chemical literature to date. Following the same published procedure, subsequent conversion of the chloro-bisphosphonate to the azido-bisphosphonate, and then the amino-bisphosphonate, takes place in high yield (80-99%) and with minimal purification required. It is worthy to note that for the amino-bisphosphonate, absolute ethanol was utilized as the solvent (rather than ethyl acetate as published).

Synthesis of [4-chloro-1-[[(1,1-dimethylethyl)dimethylsilyl]oxy]butylidene]bis-phosphonic acid tetraethyl ester (chloro-bisphosphonate)

1) P(OEt)$_3$, 0 C. → RT, 1 h
2) PH(OEt)$_2$, CH$_2$Cl$_2$, RT, 3 h
3) TBSCl, DMAP, RT, 18 h
14%

Under an atmosphere of argon, triethylphosphite (40 mL, 0.23 mol) was added dropwise to a 0° C. solution of neat 4-chlorobutyryl chloride (25 mL, 0.23 mol), via dropping funnel over a period of 30 minutes. The ice bath was removed, and the mixture was let to stir for an additional 30 minutes at room temperature, then diluted with anhydrous dichloromethane (800 mL) via cannula transfer. Diethylphosphite (29 mL, 0.23 mol) was then added, followed by 4-dimethylaminopyridine (28 g, 0.23 mol), and the mixture was stirred for an additional 2 hours. Finally, tert-butyldimethylsilylchloride (35 g, 0.23 mol) was added, and the mixture was let to stir overnight. The mixture was then washed with 1M HCl (2×1 L), H$_2$O (1×1 L), and brine (1×500 mL), dried with Na$_2$SO$_4$, then concentrated using a rotary evaporator. The residue was purified via column chromatography (SiO$_2$, gradient elution: 10% to 50% ethyl acetate in hexanes), to yield the chloro-bisphosphonate (retention factor ca. 0.2, 30% ethyl acetate in hexanes) as a colourless oil (16 g, 14%): $^1$H-NMR (500 MHz, CDCl$_3$) δ 0.13 (s, 6H), 0.83 (s, 9H), 1.30 (t, J=7.0 Hz, 12H), 2.07 (m, 2H), 2.16 (m, 2H), 3.49 (t, J=6.4 Hz, 2H), 4.07 (m, 8H); $^{13}$C-NMR (125 MHz, CDCl$_3$) δ 16.4, 19.0, 25.1, 27.1, 33.4, 45.4, 53.7, 64.2 (m); $^{31}$P-NMR (120 MHz, CDCl$_3$) δ 19.2.

Synthesis of [4-azido-1-[[(1,1-dimethylethyl)dimethylsilyl]oxy]butylidene]bis-phosphonic Acid Tetraethyl Ester (Azido-Bisphosphonate)

NaN$_3$, DMF
70 C., 3 h
75%

Under an atmosphere of argon, sodium azide (5.3 g, 0.081 mol), was added to a solution of chloro-bisphosphonate (16 g, 0.032 mol) in anhydrous dimethylformamide (200 mL). The mixture was heated to 75° C., and stirred for 3 hours at this temperature. Upon cooling to room temperature, the mixture was diluted with dichloromethane (500 mL), washed with a saturated aqueous solution of lithium chloride (4×500 mL), brine (250 mL), dried with $Na_2SO_4$, and then concentrated using a rotary evaporator to yield azido-bisphosphonate (12 g, 75%) as a colourless oil which was used in the next step without further purification: $^1$H-NMR (500 MHz, $CDCl_3$) δ 0.21 (s, 6H), 0.91 (s, 9H), 1.35 (t, J=7.0 Hz, 12H), 1.95-2.24 (m, 4H), 3.27 (t, J=6.4 Hz, 2H), 4.16-4.32 (m, 8H); $^{13}$C-NMR (125 MHz, $CDCl_3$) δ −2.6, 16.5, 19.0, 23.7, 25.8, 33.2, 51.8, 63.0 (m); $^{31}$P-NMR (120 MHz, $CDCl_3$) δ 20.5.

Synthesis of [4-amino-1-[[(1,1-dimethylethyl)dimethylsilyl]oxy]butylidene]bis-phosphonic Acid Tetraethyl Ester (Amino-Bisphosphonate)

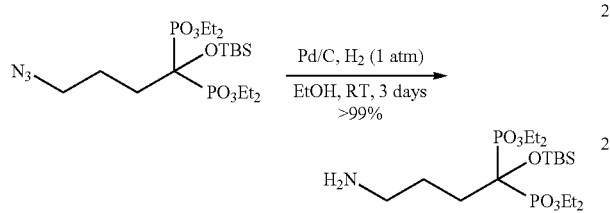

In a 1 L flask, the azido-bisphosphonate (12 g, 0.024 mol) was dissolved in absolute ethanol (500 mL), Pd/C (10 wt. %, 1.0 g) was added, and the solution was degassed for 10 minutes with hydrogen gas. The solution was stirred under an atmosphere of hydrogen for three days, and then filtered over Celite using a fritted glass funnel. The Celite was washed with additional dichloromethane (500 mL), and the filtrate was concentrated using a rotary evaporator to yield amino-bisphosphonate (11 g, >99%) as a colourless oil, which could be used as is or further purified via column chromatography ($SiO_2$, gradient elution: 10% to 100% methanol in dichloromethane): $^1$H-NMR (500 MHz, $CDCl_3$) δ 0.15 (s, 6H), 0.87 (s, 9H), 1.35 (q, J=6.8 Hz, 12H), 1.95-2.23 (m, 4H), 2.98 (br, 2H), 4.20 (m, 8H), 8.05 (br, 2H); $^{13}$C-NMR (125 MHz, $CDCl_3$) δ −2.2, 16.5, 19.0, 22.8, 25.8, 33.2, 40.4, 63.9, 64.1; $^{31}$P-NMR (120 MHz, $CDCl_3$) δ 19.5.

Synthesis of PNP-Stereate

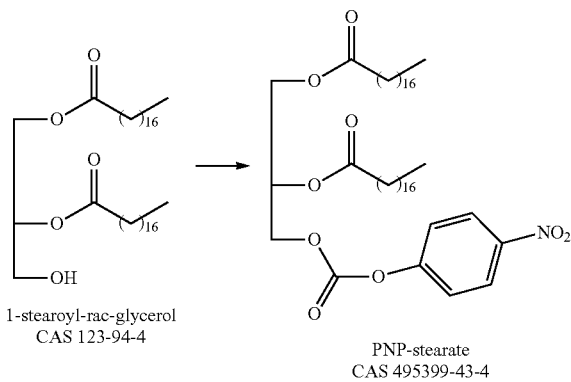

1-stearoyl-rac-glycerol
CAS 123-94-4

PNP-stearate
CAS 495399-43-4

Lab Supplies

Reagents (to Make Ca. 10 g of PNP-Stearate)
  1-Stearoyl-rac-glycerol (Aurum Pharmatech A-7346, 10 g bottle)
  para-Nitrophenyl chloroformate (Aldrich 160210, 25 g bottle but will only use 3.9 g)
  Triethylamine (Aldrich T0886, 100 mL bottle but will only use 3.4 mL)
  Dichloromethane, anhydrous (Aldrich 270997, 1 L bottle but will only use 150 mL)

Additional Lab Supplies and Materials
  Ethyl acetate
  Hexanes
  Silica gel
  Argon gas Procedure Synthesis of 3-(((4-nitrophenoxy)carbonyl)oxy)propane-1,2-diyl Distearate (PNP-Stearate)

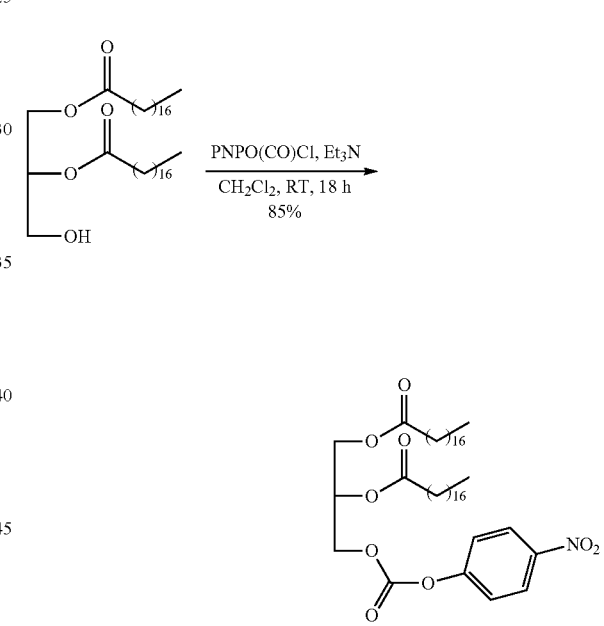

Under an atmosphere of argon, para-nitrophenyl chloroformate (3.9 g, 0.019 mol) was added to a 0° C. solution of 1-stearoyl-rac-glycerol (10 g, 0.016 mol) and triethylamine (3.4 mL, 0.024 mol) in anhydrous dichloromethane (150 mL). After stirring for ten minutes, the ice bath was removed, and the mixture was let to stir at room temperature overnight. The mixture was then concentrated using a rotary evaporator, and the residue was purified via column chromatography ($SiO_2$, eluent 10% ethyl acetate in hexanes), to yield PNP-stearate (retention factor ca. 0.4, 10% ethyl acetate in hexanes) as a white powder (11 g, 85%): $^1$H-NMR (500 MHz, $CDCl_3$) δ 0.88 (t, J=7 Hz, 6H), 1.18-1.35 (m, 56H), 1.62 (m, 4H), 2.34 (m, 4H), 4.22 (dd, J=12, 6 Hz, 1H), 4.36 (m, 2H), 4.49 (dd, J=12, 4 Hz, 1H), 5.37 (m, 1H), 7.39 (m, 2H), 8.29 (m, 2H); $^{13}$C-NMR (125 MHz, $CDCl_3$) δ 173.3, 172.9, 155.3, 152.3, 145.5, 125.4, 121.8, 68.3, 67.0, 61.6, 34.2, 34.0, 29.7, 29.5, 29.4, 29.3, 29.1, 24.5, 22.7, 14.2.

Synthesis of PEG3000-Stearoyl-Bisphosphonate (GL-3000S)

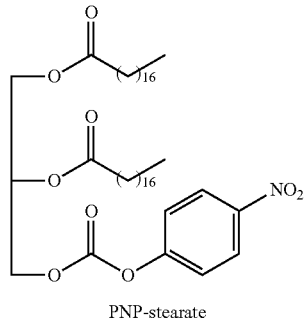

PNP-stearate

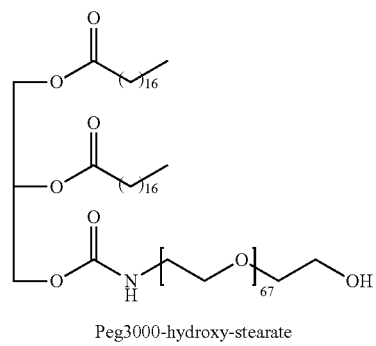

Peg3000-hydroxy-stearate

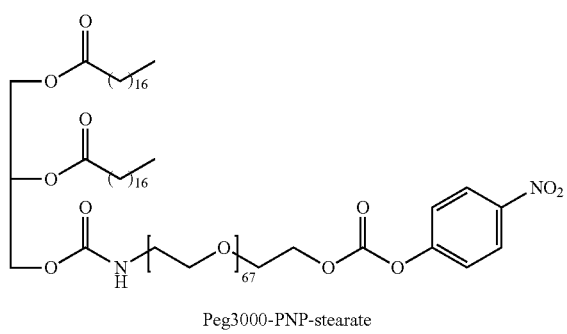

Peg3000-PNP-stearate

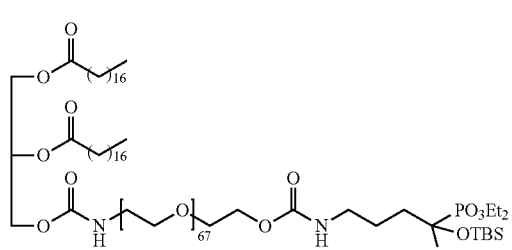

Peg3000-stearoyl-bisphonsphonate ester

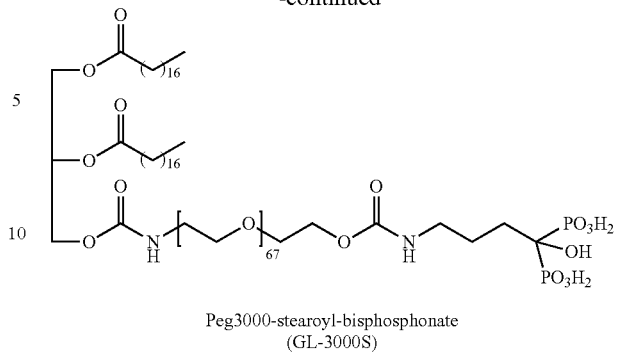

Peg3000-stearoyl-bisphosphonate (GL-3000S)

Lab Supplies

Reagents (to Make Ca. 7 g of PEG3000-Stearoyl-Bisphosphonate)
PNP-stearate (synthesized as described in Section 2, 2.4 g)
O-(2-Aminoethyl)polyethylene glycol 3,000 (BOC Sciences 32130-27-1 or Aldrich 07969, 6 g)
Triethylamine (Aldrich T0886, 100 mL bottle but will only use 1.7 mL)
Dichloromethane, anhydrous (Aldrich 270997, 1 L bottle but will only use 400 mL)
para-Nitrophenyl chloroformate (Aldrich 160210, 25 g bottle but will only use 0.61 g)
Amino-bisphosphonate (synthesized as described in Section 1, 1.4 g)
Bromotrimethylsilane (Aldrich 194409, 25 g bottle but will only use 2.3 mL)
2,6-Lutidine (Aldrich L3900, 100 mL bottle but will only use 3.2 mL)

Additional Lab Supplies and Materials
Diethyl ether
Dichloromethane
Methanol
Celite filter aid
Deuterated chloroform

Procedure

Synthesis of PEG3000-Hydroxy-Stearate

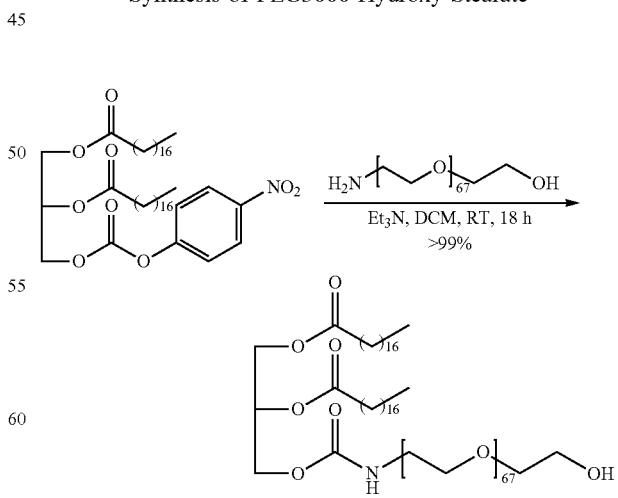

O-(2-Aminoethyl)polyethylene glycol 3,000 (6 g, 2 mmol) was added to a room temperature solution of PNP-stearate (2.4 g, 3 mol) and triethylamine (0.55 mL, 4 mol) in anhydrous dichloromethane (100 mL), and let to stir overnight. The mixture was then concentrated using a rotary evaporator, and the residue was triturated with diethyl ether (1 L), with stirring for three hours at room temperature. The resulting white solid was filtered over Celite using a fritted funnel, and the filter cake washed profusely with diethyl ether (4×250 mL). The filter cake was suspended in dichloromethane, re-filtered into a clean collecting flask, and then washed with additional dichloromethane (2×250 mL). The dichloromethane washes were then combined, and concentrated using a rotary evaporator, to yield PEG3000-hydroxystearate as a white powder (7.3 g, >99%): $^1$H-NMR (500 MHz, CDCl$_3$) δ 0.85 (t, J=7 Hz, 6H), 1.15-1.32 (m, 56H), 1.58 (m, 4H), 2.29 (m, 4H), 3.31-3.83 (m, 272H), 4.15 (m, 2H), 4.23 (m, 2H), 5.13 (m, 1H), 5.31 (m, 1H).

Synthesis of PEG3000-PNP-Stearate

The mixture was then concentrated using a rotary evaporator, and the residue was triturated with diethyl ether (1 L), with stirring for three hours at room temperature. The resulting white solid was filtered over Celite using a fritted funnel, and the filter cake washed profusely with diethyl ether (4×250 mL). The filter cake was suspended in dichloromethane, re-filtered into a clean collecting flask, and then washed with additional dichloromethane (2×250 mL). The dichloromethane washes were then combined, and concentrated using a rotary evaporator, to yield PEG3000-PNP-stearate as a white powder (7.7 g, >99%): $^1$H-NMR (500 MHz, CDCl$_3$) δ 0.84 (t, J=7 Hz, 6H), 1.16-1.50 (m, 56H), 1.57 (m, 4H), 2.28 (m, 4H), 3.30-3.80 (m, 271H), 4.14 (m, 2H), 4.21 (m, 2H), 4.41 (m, 1H), 5.11 (m, 1H), 5.33 (m, 1H), 7.36 (m, 2H), 8.25 (m, 2H).

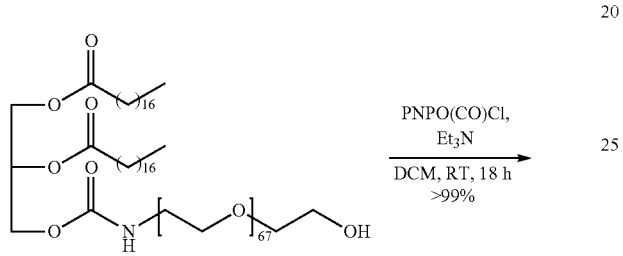

Synthesis of PEG3000-Stearoyl-Bisphosphonate Ester

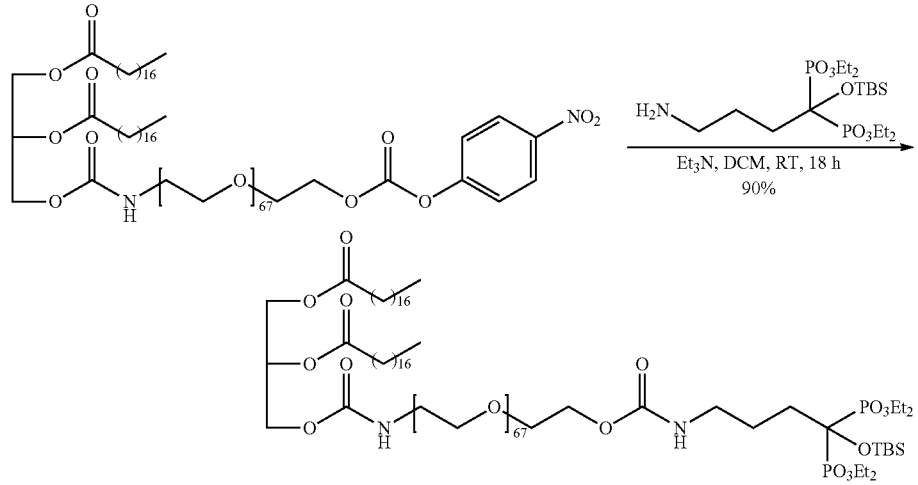

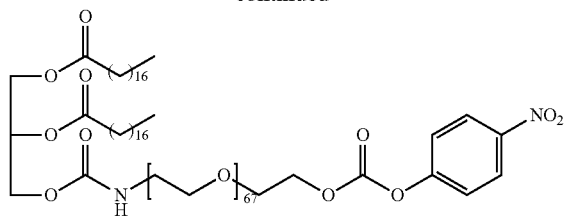

Para-nitrophenyl chloroformate (0.61 g, 3 mmol) was added to a room temperature solution of PNP-stearate (7.3 g, 2 mmol) and triethylamine (0.55 mL, 4 mmol) in anhydrous dichloromethane (100 mL), and let to stir overnight.

A solution of amino-bisphosphonate (1.4 g, 3 mmol) in anhydrous dichloromethane (5 mL) was added to a room temperature solution of PEG3000-PNP-stearate (7.7 g, 2 mmol) and triethylamine (0.55 mL, 4 mmol) in anhydrous dichloromethane (100 mL), and let to stir overnight. The mixture was then concentrated using a rotary evaporator, and the residue was triturated with diethyl ether (1 L), with stirring for three hours at room temperature. The resulting white solid was filtered over Celite using a fritted funnel, and the filter cake washed profusely with diethyl ether (4×250 mL). The filter cake was suspended in dichloromethane, re-filtered into a clean collecting flask, and then washed with additional dichloromethane (2×250 mL). The dichloromethane washes were then combined, and concentrated using a rotary evaporator, to yield PEG3000-stearoylbisphosphonate ester as a white powder (7.6 g, 90%): $^1$H-NMR (500 MHz, CDCl$_3$) δ 0.17 (s, 6H), 0.87 (t, J=7 Hz, 6H), 0.88 (s, 9H), 1.20-1.29 (m, 56H), 1.33 (t, J=7 Hz, 12H), 1.59 (m, 4H), 1.85 (m, 2H), 2.03 (m, 2H), 2.29 (m, 4H), 3.15 (m, 2H), 3.30-3.82 (m, 272H), 4.08-4.33 (m, 12H), 4.88 (m, 1H), 5.23 (m, 1H), 5.33 (m, 1H). $^{31}$P-NMR (120 MHz, CDCl$_3$) δ 19.5.

Synthesis of PEG3000-Stearoyl-Bisphosphonate (GL-3000S)

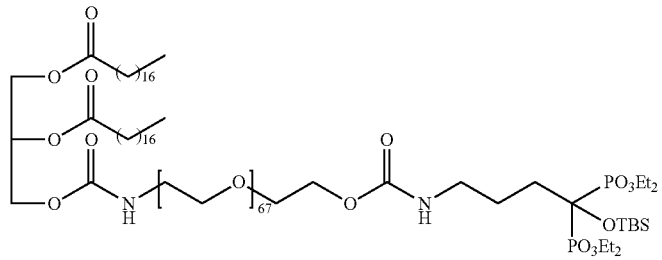

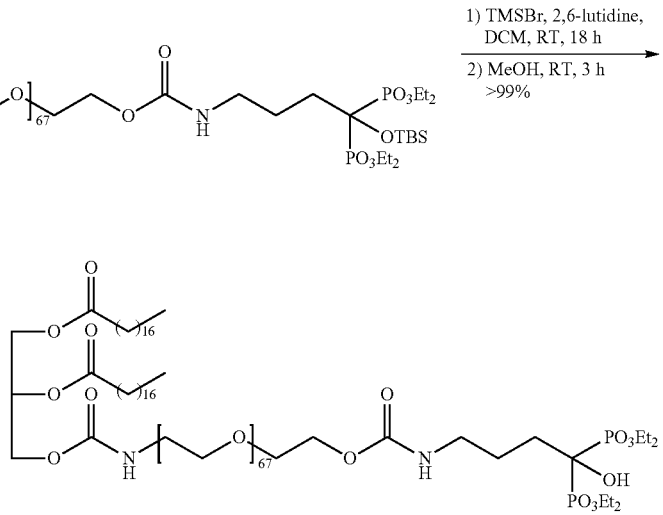

Under an atmosphere of argon, bromotrimethylsilane (2.3 mL, 18 mmol) was added to a room temperature solution of PEG3000-stearoyl-bisphosphonate ester (7.6 g, 1.8 mmol) and 2,6-lutidine (3.2 mL, 27 mmol) in anhydrous dichloromethane (100 mL), and let to stir overnight. The mixture was then concentrated using a rotary evaporator, the residue was dissolved in methanol (150 mL), and stirred an additional 3 hours at room temperature. The mixture was again concentrated using a rotary evaporator, and the residue was triturated with diethyl ether (1 L), with stirring for three hours at room temperature. The resulting white solid was filtered over Celite using a fritted funnel, and the filter cake washed profusely with diethyl ether (4×250 mL). The filter cake was suspended in dichloromethane, re-filtered into a clean collecting flask, and then washed with additional dichloromethane (2×250 mL). The dichloromethane washes were then combined, concentrated using a rotary evaporator, and dried under high vacuum (100 mtorr) for 24 hours to yield PEG3000-stearoyl-bisphosphonate as a white powder (7.1 g, >99%): $^1$H-NMR (500 MHz, CDCl$_3$) δ 0.91 (t, J=7 Hz, 6H), 1.19-1.51 (m, 56H), 1.63 (m, 4H), 2.05 (m, 2H), 2.20 (m, 2H), 2.33 (m, 4H), 2.90 (m, 2H), 3.22-3.94 (m, 272H), 4.10-4.40 (m, 4H), 4.86 (m, 1H), 5.27 (m, 1H), 5.40 (m, 1H); $^{31}$P-NMR (120 MHz, CDCl$_3$) δ 19.0. *Note that at this stage, the product still contains a variable amount of 2,6-lutidine (ca. 20-50 mol %, as determined by integration of the corresponding $^1$H-NMR peaks at 7.4, 6.9, and 2.5 ppm). This impurity can be removed entirely by dialysis using Spectra/Por Dialysis tubing (1 kDa, 10 mm flat width) and methanol as the solvent, however this was found to decrease the overall yield to 20-40%.

Example 2: Synthesis of VMM-iv93

VMM-iv93, and in general, compounds of the present disclosure were synthesized according to the chemical synthesis method as outlined below:

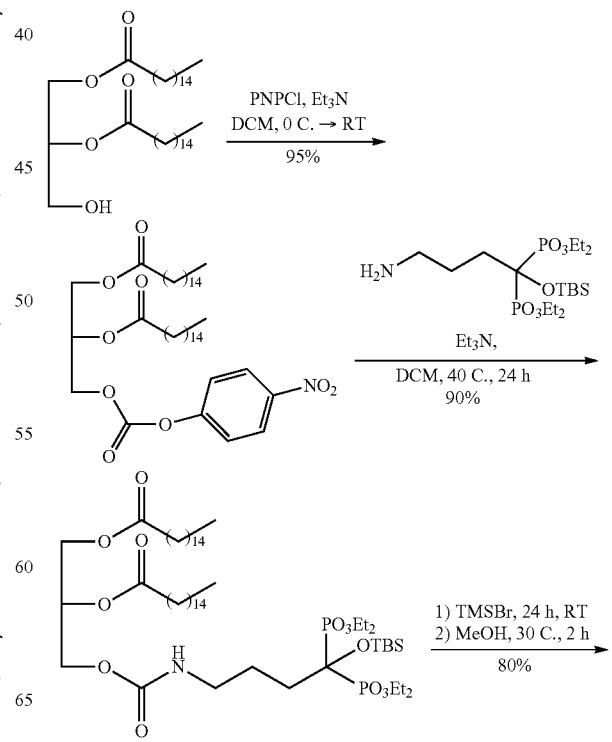

-continued

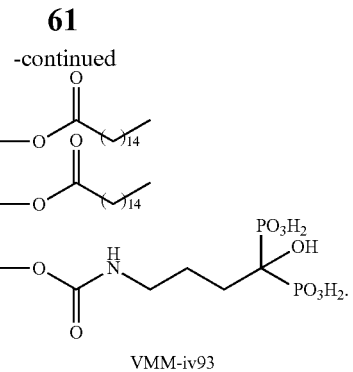

VMM-iv93

Synthesis of VMM-iv93 from this reaction was confirmed by 2D NMR methods as well as mass spectrometry.

Example 3: Synthesis of VMM-iv95

VMM-iv95 was synthesized according to the chemical synthesis method as outlined above.

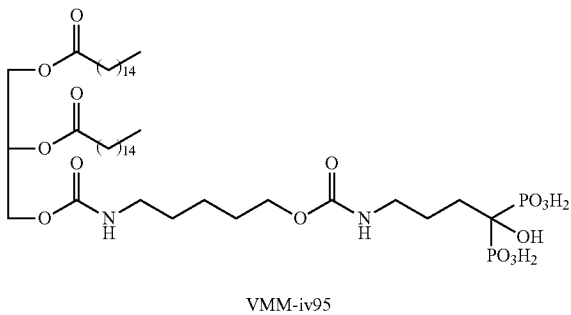

VMM-iv95

Synthesis of VMM-iv95 from this reaction was confirmed by 2D NMR methods as well as mass spectrometry.

Example 4: Experimental Procedure For Microbubble Synthesis

Stock solutions of DPPC (200 mg) in chloroform (20 mL), and DPPA (20 mg) in chloroform (2 mL), were created through dissolving the lipid via gentle shaking and heating. Upon cooling to room temperature, 0.9 mL of the DPPC solution and 0.1 mL of the DPPA solution were transferred to a 40 mL vial. The chloroform was evaporated, and then 10 mL of a solution of 0.1 M PBS:glycerol:propylene glycol (80:10:10) was added to the vial. The lipid components dissolved upon heating this mixture to 60° C. for 1 h. Upon cooling to room temperature, the vial was then purged for ca. 60 seconds with fluorocarbon gas, e.g., perfluorobutane gas. The vial was then agitated (using vial mix) for at least 60 s. This procedure (purging/agitation) was repeated 3 times, until the solution appeared opaque.

Example 5: Synthesis of Microbubbles and Size Assay

Microbubbles were synthesized according to a slight modification of the Definity procedure, as well as that of Feshitan et. al (Journal of Colloid and Interface Science, 2009, 329, 316-324). Five different types of microbubble solutions were made, each containing: [A] DPPC:DPPA in a 9:1 ratio; [B] DPPC:VMM-iv93 in a 9:1 ratio; [C] DPPC: VMM-iv95 in a 9:1 ratio; [D] VMM-iv93 ONLY; [E] VMM-iv95 ONLY. Microbubble solution [A] was synthesized as a "control" sample for experiments testing attachment of compositions comprising VMM-iv93 and VMM-iv95, to kidney stones. "BLANK" A solution was also prepared using the entire synthesis and components described herein, except fluorocarbon gas was not added. Therefore, any microbubbles presents in solution are expected to be filled with air, and not expected to be stable.

Figure 1B:
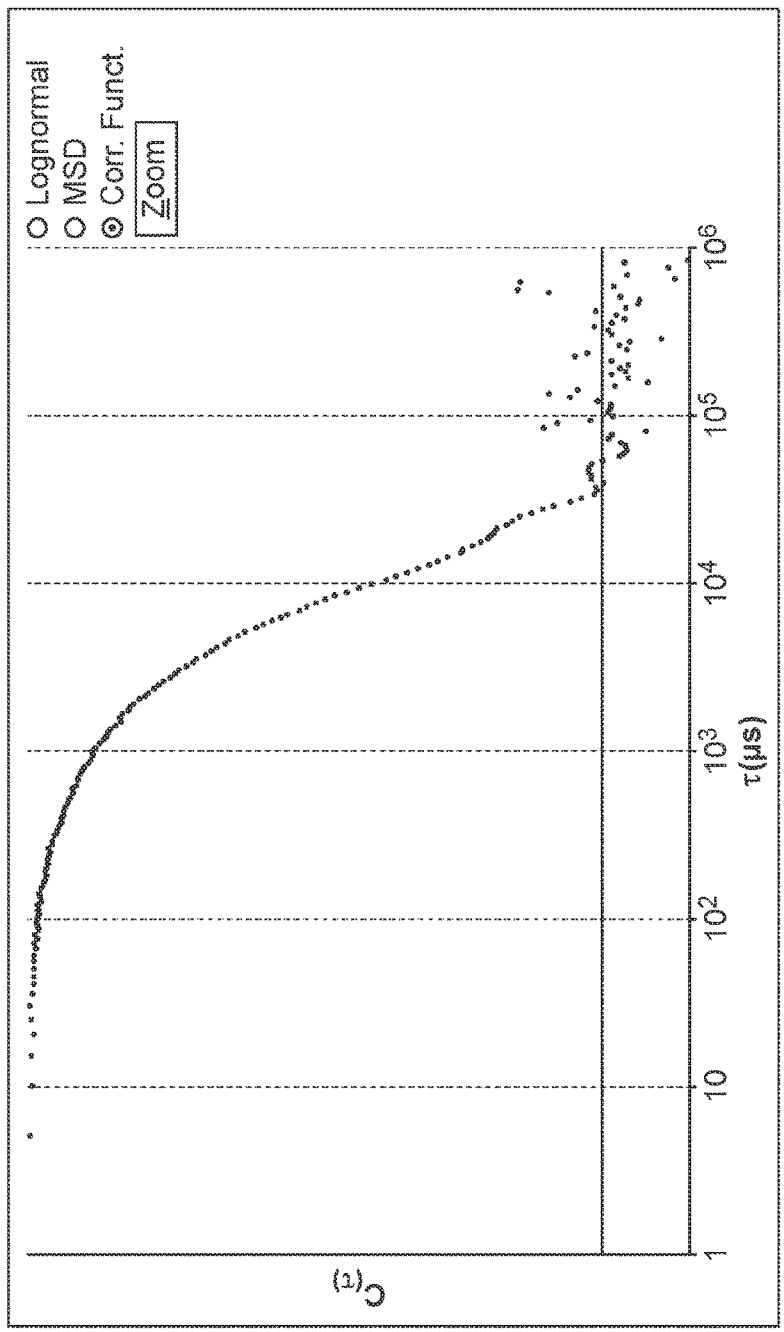

Formation of microbubbles was confirmed with dynamic light scattering (DLS). The experiment showed that crude solutions from the synthesis include microbubbles of 2-4 μm diameters, as expected based on the literature. For example, as represented in FIG. 1, formation of microbubbles of 2-4 μm diameters was detected in Solution D. However, microbubbles were not detected in "Blank" A. Table 1 represents an average of what was present in the solutions however, in general, particle size distribution was broad.

TABLE 1

| Solution | Components | Particle Size (μm) |
| --- | --- | --- |
| "BLANK" A | 9:1 DPPC:DPPA (no fluorocarbon gas) | 0 |
| A | 9:1 DPPC:DPPA | 3 |
| B | 9:1 DPPC:VMM-iv93 | 2 |
| C | 9:1 DPPC:VMM-iv95 | 3 |
| D | VMM-iv93 | 2 |
| E | VMM-iv95 | 2 |

Figure 2A:
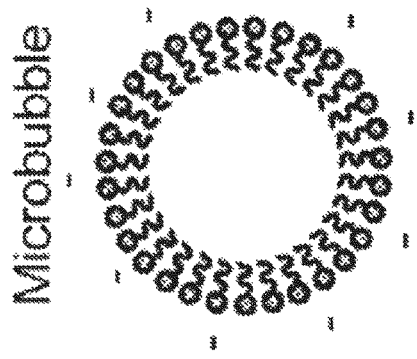
FIG. 2A is an exemplary illustration of a microbubble formed with fatty-acid glycerol ester derivative compounds.
Figure 2B:
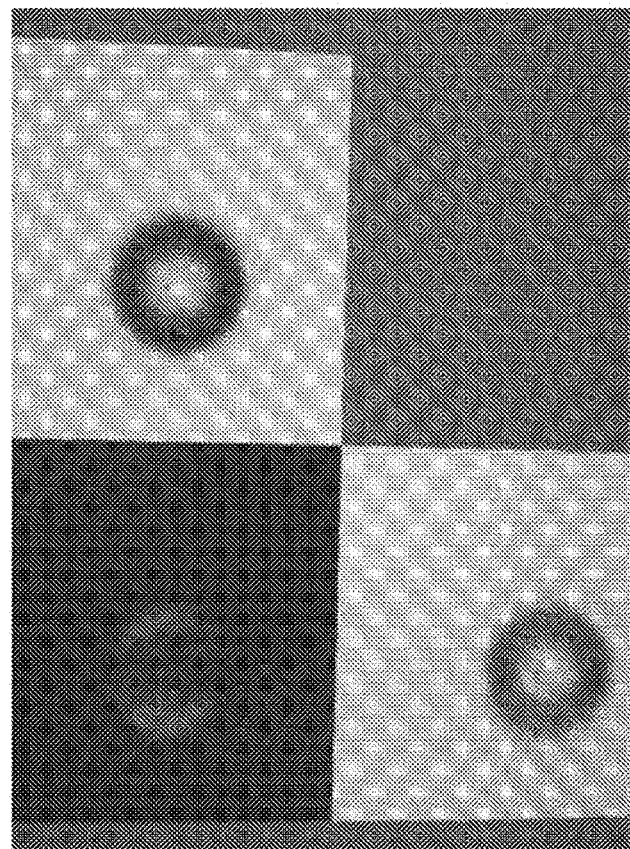
FIG. 2B is laser-scanning fluorescence confocal microscopy images of a microbubble formed in Solution D (VMM-iv93).

Microbubble formation was also confirmed via laser-scanning fluorescence confocal microscopy. Size range of 2-4 μm, as measured by DLS, was also confirmed for all solutions. For example, FIG. 2 B represents laser-scanning fluorescence confocal microscopy images of a microbubble formed in Solution D (VMM-iv93).

Example 6: In-Vitro Visualization of Stone Attachment Using Hydrophilic Fluorescent Dyes Synthesized microbubbles were "labelled" with hydrophobic fluorescent dyes, which are commonly used for staining lipid membranes in cells. It is well known in the art that the fluorescent dyes fluoresce weakly in water but strongly when incorporated in lipid bilayers. They have been used for other microbubble applications in the literature (drug delivery, etc.), in order to visualize the microbubbles using confocal microscopy. They have been shown to integrate into gas-filled microbubbles, without disrupting the microbubbles. As in the literature, microbubbles were labelled by adding in the dye directly before the addition of fluorocarbon gas.

As expected, solution A, i.e., 9:1 DPPC:DPPA, showed no microbubbles labelled with DiO before the addition of fluorocarbon gas (i.e., "BLANK" A). However, after the addition of fluorocarbon gas, solution A showed 3 m microbubbles labelled with DiO or DiI.

Several kidney stones were then dipped into these solutions, and then removed for analysis of targeted binding. The stones were allowed to dry for ca. 1 minute, before washing with 0.1 M PBS:glycerol:propylene glycol (80:10:10) solution, which was done to remove any unbound bubbles or dye.

Kidney stones showed no staining when reacted with Solution A (9:1 DPPC:DPPA bubbles), labelled with DiI, because DPPC:DPPA bubbles do not bear any targeting bisphosphonate group. Kidney stones showed strong staining with DiI when reacted with Solution C (9:1 DPPC: VMM-iv95) or Solution E (VMM-iv95 only), labelled with DiI. Staining by Solution C and Solution E was detected with naked eyes as well as through imaging via laser-scanning fluorescence confocal microscopy.

Figure 3A:
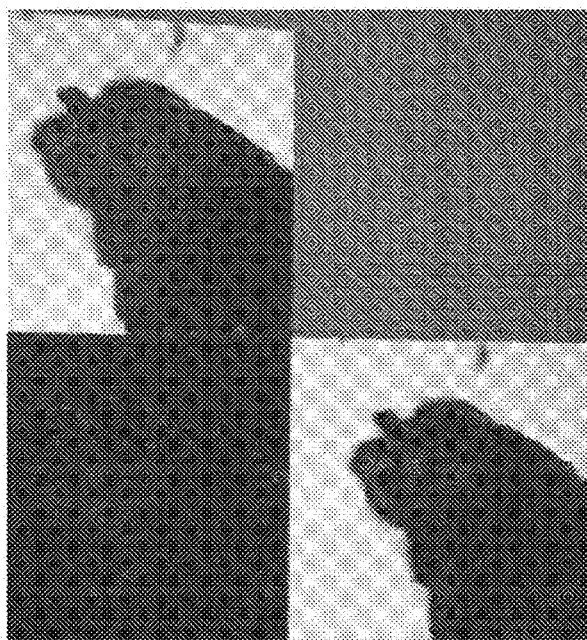
FIGS. 3A and 3B are laser-scanning fluorescence confocal microscopy images of kidney stones reacted with different compositions.
Figure 3B:
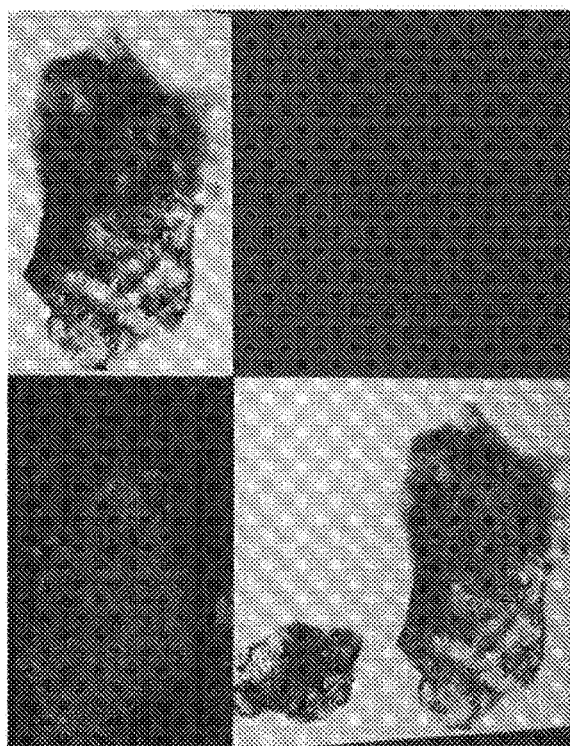

FIG. 3 provides some laser-scanning fluorescence confocal microscopy images of kidney stones reacted with different compositions. FIG. 3. A is images of a kidney stone reacted with microbubbles formed with Solution A (9:1 DPPC:DPPA) and labelled with DiI. The images show limited staining of the stone. FIG. 3. B is images of a kidney stone reacted with microbubbles formed with Solution E (VMM-iv95) and labelled with DiI. The images show stronger staining of the stone.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

We claim:

1. A compound of a formula, the formula selected from the group consisting of formula (I), formula (Ia), formula (II), formula (III), formula (IV) and formula (V):

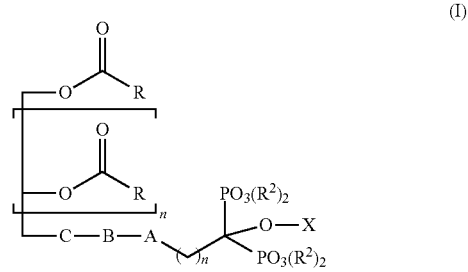

(I)

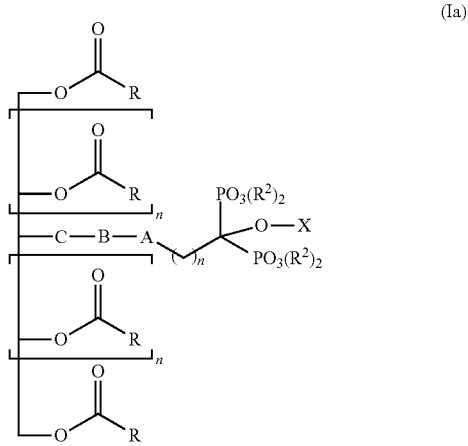

(Ia)

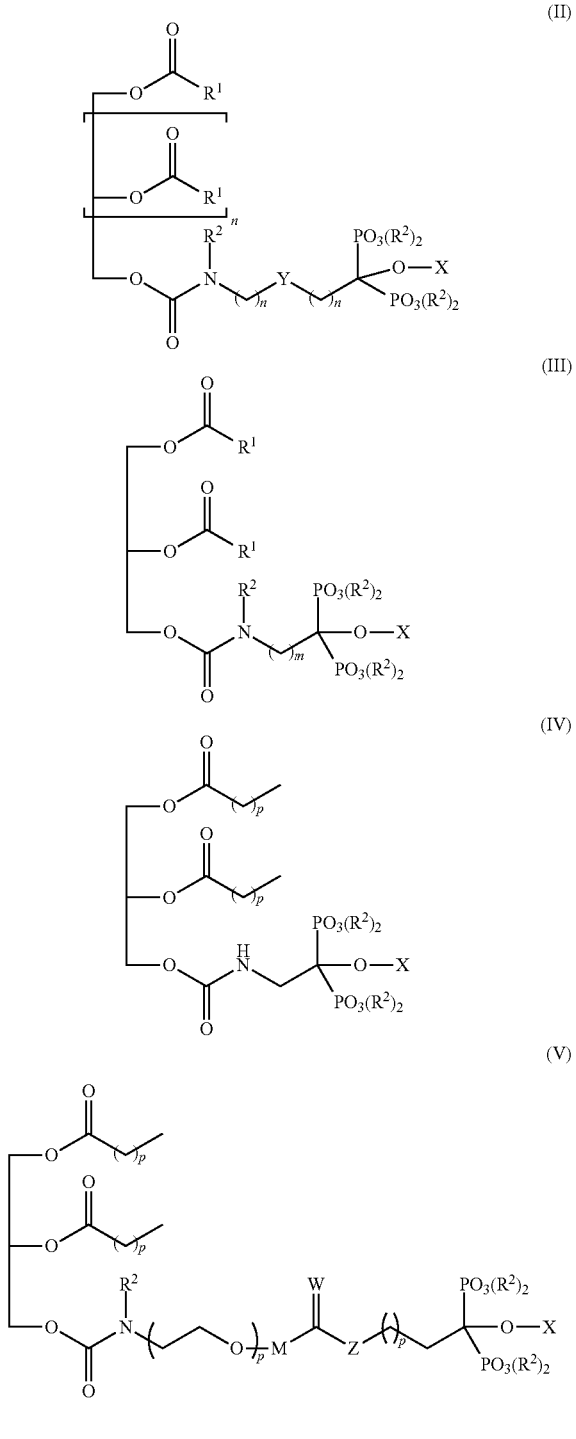

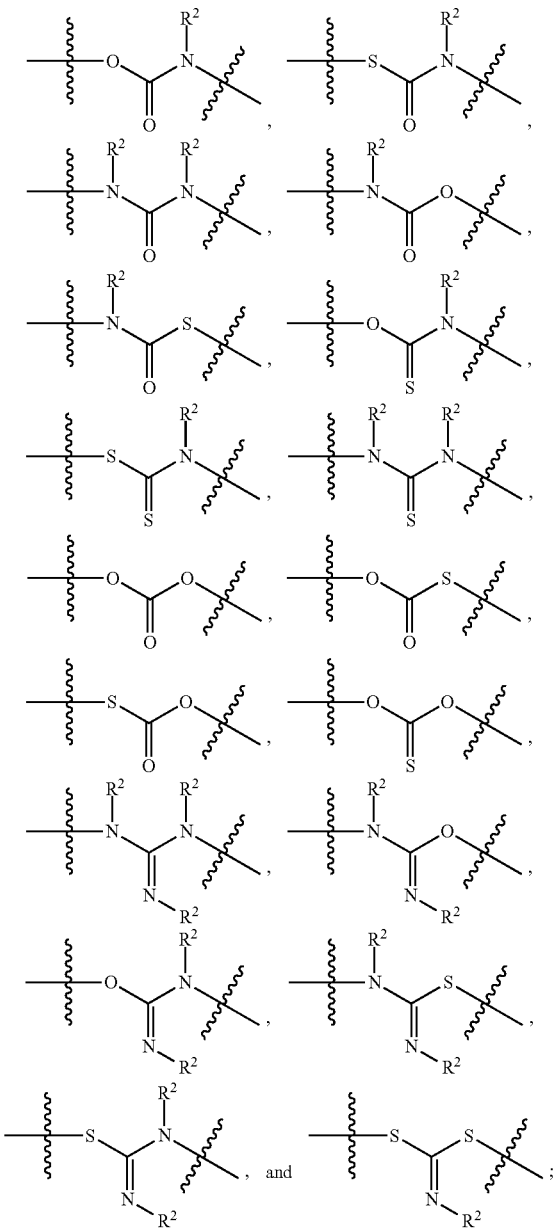

each $R^2$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl, $C_3$-$C_8$ cycloalkyl, $C_3$-$C_8$ substituted cycloalkyl, $C_3$-$C_8$ aryl, $C_3$-$C_8$ substituted aryl, $C_3$-$C_8$ heterocycloalkyl, $C_3$-$C_8$ substituted heterocycloalkyl, $C_3$-$C_8$ heteroaryl, $C_3$-$C_8$ substituted heteroaryl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

C is selected from the group consisting of:

wherein:
each n is independently selected from 0-7;
each m is independently selected from 0-26;
each p is independently selected from 7-26;
each q is independently selected from 1-90;
each $R^1$ is independently selected from the group consisting of: hydrogen, $C_1$-$C_{26}$ alkyl, $C_1$-$C_{26}$ substituted alkyl, $C_1$-$C_{26}$ alkenyl, $C_1$-$C_{26}$ substituted alkenyl, $C_1$-$C_{26}$ alkynyl, $C_1$-$C_{26}$ substituted alkynyl, $C_1$-$C_{26}$ alkyl aryl, $C_1$-$C_{26}$ substituted alkyl aryl, $C_1$-$C_{26}$ alkenyl aryl, $C_1$-$C_{26}$ substituted alkenyl aryl, $C_1$-$C_{26}$ alkynyl aryl, $C_1$-$C_{26}$ substituted alkynyl aryl;

B is selected from the group consisting of: a covalent bond, ethylene glycol, and polyethylene glycol;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester, wherein any of these functional groups listed for A may be covalently bonded on either side to the

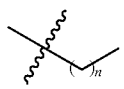

moiety;

Y is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester, wherein any of these functional groups listed for A may be covalently bonded on either side to either one of the

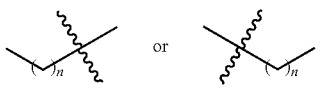

moieties;

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$;

W is selected from the group consisting of: O, $NR_2$, and S;

Z is selected from the group consisting of: a covalent bond, $CH_2$, O, $NR_2$, and S;

M is selected from the group consisting of: a covalent bond, $CH_2$—$CH_2$, $CH_2$—$CH_2$—Z, $CH_2$—Z and $CH_2$;

or a tautomer and/or a pharmaceutically acceptable salt thereof.

2. The compound of claim 1, wherein the formula is the formula (II).

3. The compound of claim 1, wherein the formula is the formula (III).

4. The compound of claim 1, wherein the formula is the formula (IV).

5. The compound of claim 1, wherein the formula is the formula (V).

6. The compound of claim 1 selected from the group consisting of:

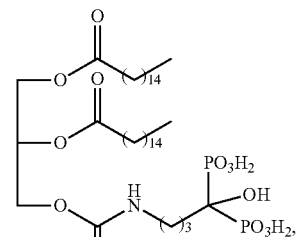

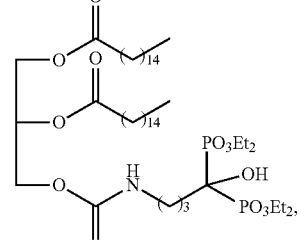

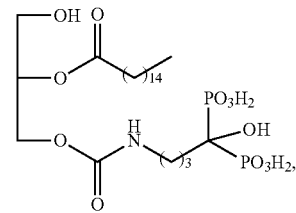

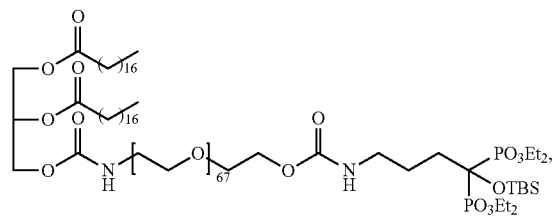

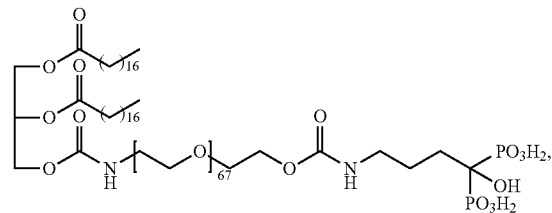

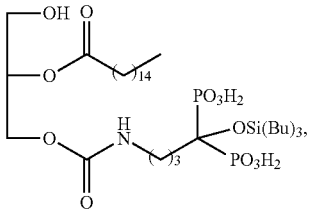

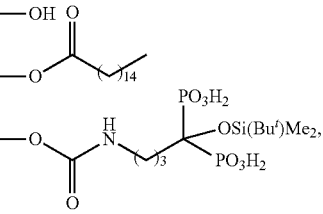

-continued
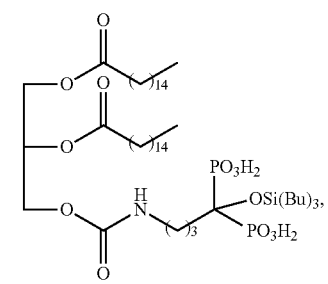
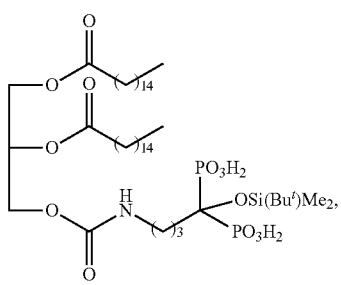
-continued
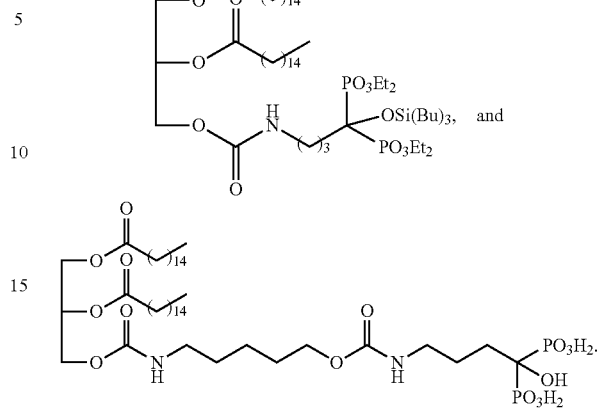
7. The compound of claim 4, wherein each p is independently selected from 14-22; X is silyl, and each R2 is hydrogen or C1-C8 alkyl.
8. The compound of claim 1, wherein the formula is the formula (I) or the formula (Ia).
* * * * *

UNITED STATES PATENT AND TRADEMARK OFFICE
CERTIFICATE OF CORRECTION

PATENT NO. : 10,945,946 B2
APPLICATION NO. : 16/831781
DATED : March 16, 2021
INVENTOR(S) : Marx et al.

Page 1 of 1

It is certified that error appears in the above-identified patent and that said Letters Patent is hereby corrected as shown below:

In the Claims

Column 65, Lines 52 and 53, Claim 1, delete "  " and insert -- 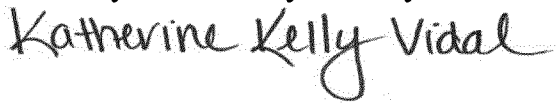 --.

Signed and Sealed this
Twenty-fourth Day of May, 2022

Katherine Kelly Vidal
Director of the United States Patent and Trademark Office